United States Patent [19]
Barone

[11] Patent Number: 6,162,246
[45] Date of Patent: Dec. 19, 2000

[54] AORTIC GRAFT AND METHOD OF TREATING ABDOMINAL AORTIC ANEURYSMS

[76] Inventor: Hector Daniel Barone, Maza 1948, Buenos Aires 1240, Argentina

[21] Appl. No.: 09/250,742

[22] Filed: Feb. 16, 1999

[51] Int. Cl.[7] .................................................. A61F 2/06
[52] U.S. Cl. ................................... 623/1.35; 623/1.1
[58] Field of Search ................................ 623/1.35, 1.11, 623/1.51, 12, 1; 128/898; 606/194, 108, 191, 198, 195; 604/96

[56] References Cited

U.S. PATENT DOCUMENTS

| | | |
|---|---|---|
| 4,562,596 | 1/1986 | Kornberg . |
| 4,922,905 | 5/1990 | Strecker . |
| 5,575,817 | 11/1996 | Martin ........................................... 623/1 |
| 5,609,627 | 3/1997 | Goicoechea et al. ......................... 623/1 |
| 5,628,788 | 5/1997 | Pinchuk . |
| 5,632,772 | 5/1997 | Alcime . |
| 5,639,278 | 6/1997 | Dereume . |
| 5,676,696 | 10/1997 | Marcade ....................................... 623/1 |

FOREIGN PATENT DOCUMENTS

| | | |
|---|---|---|
| 8303752 | 11/1983 | WIPO . |
| 9015582 | 12/1990 | WIPO . |

*Primary Examiner*—Michael Buiz
*Assistant Examiner*—Anthony King
*Attorney, Agent, or Firm*—Norris, McLaughlin & Marcus P.A.

[57] ABSTRACT

An aortic graft and method for treatment of abdominal aortic aneurysms by inserting into the aorta and into the iliac arteries of the patient the graft in a way to exclude the aneurysm from the blood circulatory system, the graft comprising a tubular hollow fabric material including a trunk portion and at least one leg portion capable of being accommodated to any rotation of the graft resulting from the installation of the graft and to any varying ratio between the diameters of an aortic neck and the iliac arteries, the graft being also adapted to different shapes of the aorta, thus diminishing and even avoiding the risks of misplacing the graft inside the aorta. The trunk also includes an inelastic edge to retain a stent in an expanded condition to attach the trunk and the leg portions together.

42 Claims, 8 Drawing Sheets

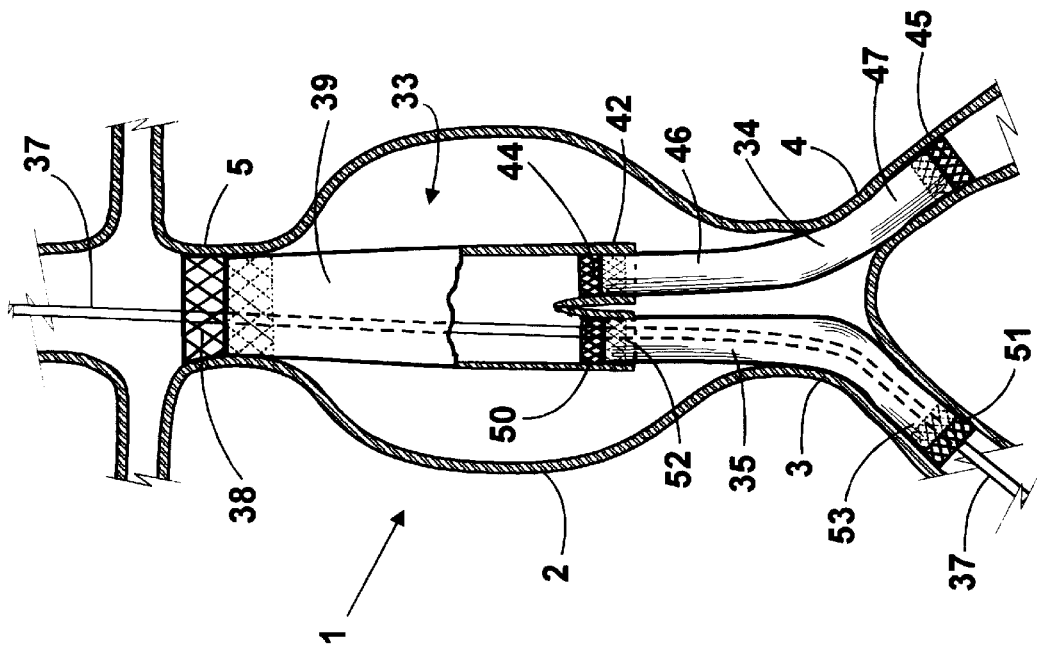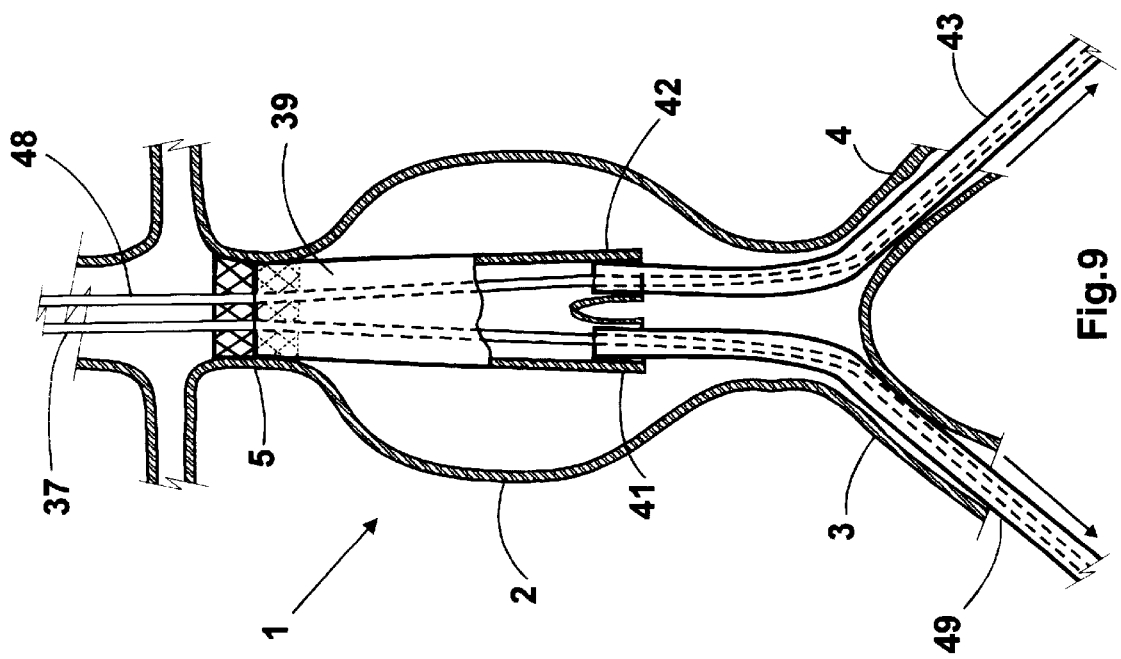

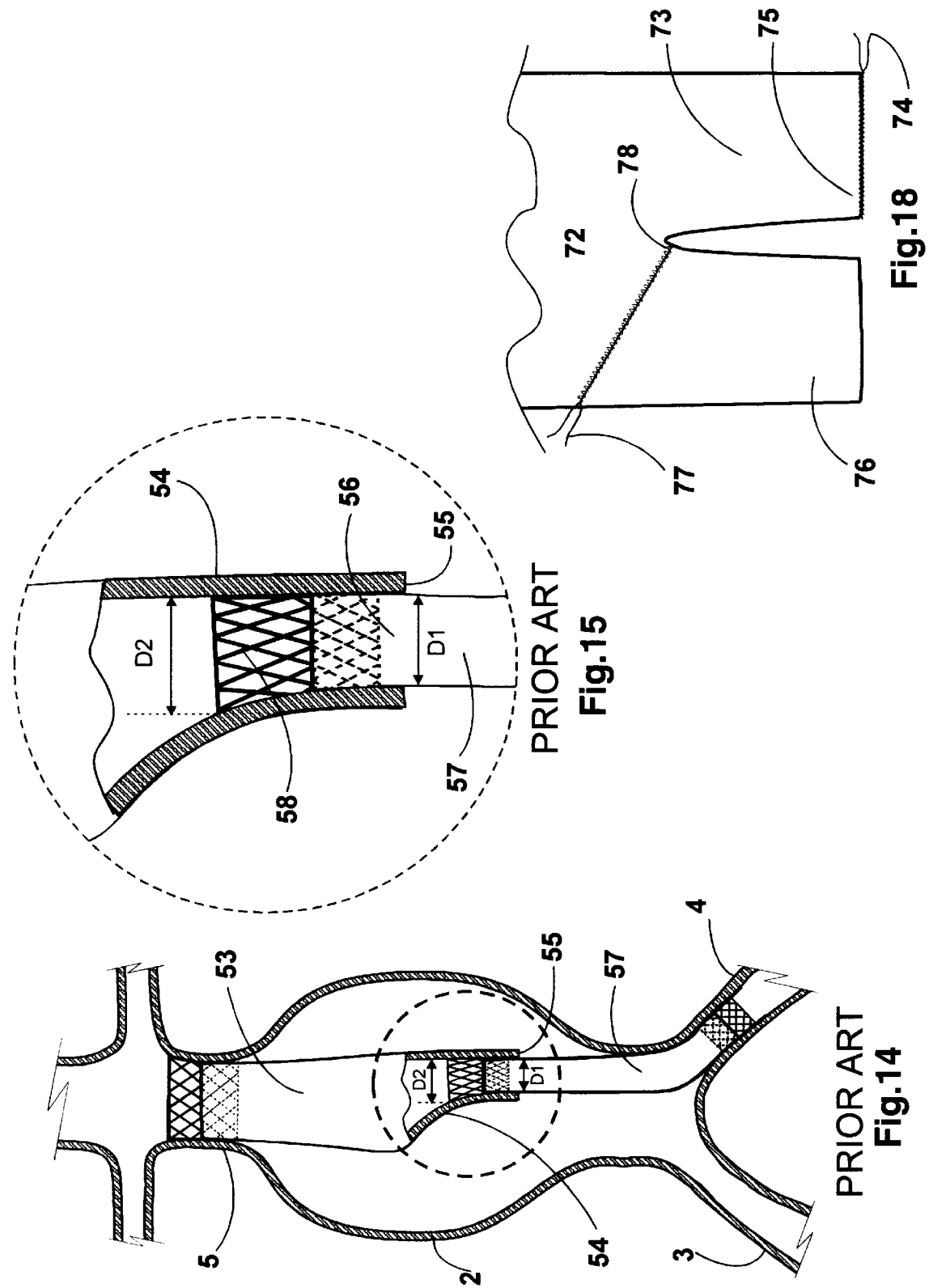

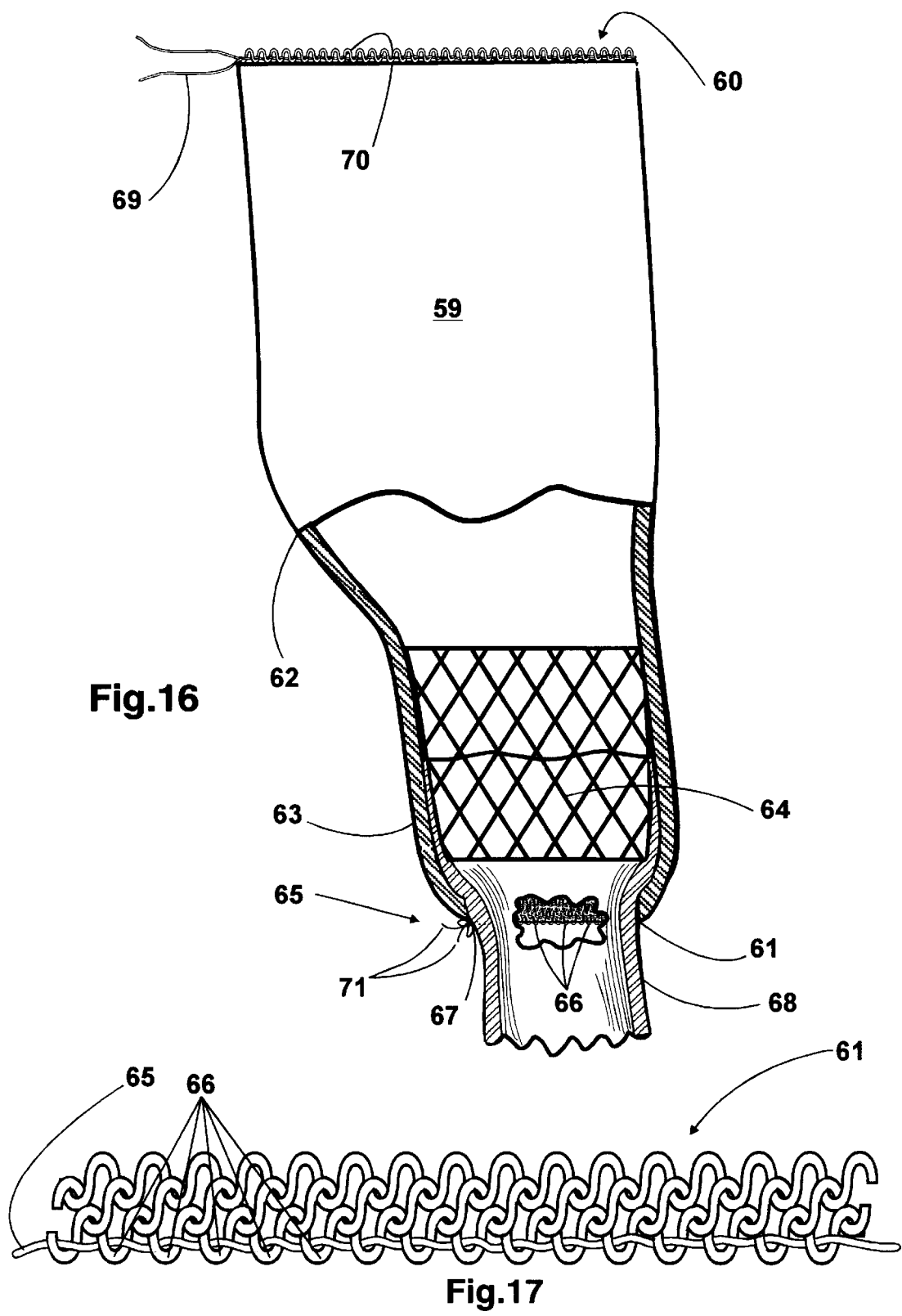

AORTIC GRAFT AND METHOD OF TREATING ABDOMINAL AORTIC ANEURYSMS

BACKGROUND OF THE INVENTION

1. Field of the Invention

The present invention relates to an aortic graft and method of treating abdominal aneurysms, and particularly relates to a graft and method for intraluminal repairing of aortic aneurysms by positioning the graft inside the aneurysm without the drawbacks of conventional monoiliac or bifurcated aorto iliac grafts, such drawbacks relating to the rotation and misplacement of the graft during the insertion, positioning and installation of the graft inside the aorta.

2. Description of the Prior Art

The aorta is the main trunk of the arterial system, arising from the heart and extending down through the thorax and through the abdomen to divide into two iliac arteries. An abdominal aortic aneurysm is an abnormal dilation of the aortic wall as the aorta passes through the abdomen. The aneurysm must be treated to prevent the rupturing thereof. If left untreated, the aneurysm will eventually cause rupture of the sac with fatal hemorrhaging consequences in a very short time. This leads to the death of the individual suffering the aneurysm and, today, the mortality resulting form this abnormality is so very high that it is causing the physicians to seek for improved new techniques to overcome this problem. While surgery has been the most classical way to approach this problem, the surgical repair of the aortic wall is associated, however, to a high risk, particularly for old patients.

The search for alternative techniques not involving surgery has been a concern of the professionals in the art. U.S. Pat. No. 4,562,596, to Elliot Kornberg et al. discloses an aortic bifurcated graft that is specifically designed for intraluminal insertion and comprising a one-piece generally cylindrical hollow sleeve, that has an upper end to be attached to an upper proximal neck of the aorta, upstream the aneurysm, and a minor and major axis defining two lower legs to be inserted each into a respective iliac artery, downstream of the aneurysm, thus forming a continuous fluid path within the aorta, excluding the affected aortic wall, namely the aneurysm, from the blood flow.

U.S. Pat. No. 4,922,905 relates to a catheter and discloses a tubular endoprosthesis device having a wall structure comprised of a tube-like, knitted open fabric of loosely interlocked loops of metallic filament material, said tube-like fabric being radially inwardly deformed relative to its as-knit form and is capable of progressive permanent deformation with attendant radial expansion by means of the catheter to attach the endoprosthesis inside a blood vessel to be repaired.

WO 83/03752 to Wallsten, Hans Ivar, discloses a prosthesis comprising a one-piece expandable tubular body to be inserted into a vascular vessel.

WO 90/15582 to Trout, Hugh, discloses an aortic graft comprising a substantially cylindrical graft material with attachment means which comprise a plurality of post and hook assemblies to provide firm attachment of the aortic graft against the aortic wall.

Although many graft structures have been developed, all of them have been improved in connection to new materials, new attachment means, stents and/or new devices for placing and installing the graft inside the vessel. However, the location and correct placing of the graft inside a blood vessel, particularly a graft designed for repairing aortic aneurysms, are not an easy task as long as the aorta is the largest vessel with a shape that requires that special consideration is made not only of the dilated wall but also of such portions of the wall in good conditions available for firmly attaching the graft in the aorta.

One obstacle that is found during election of the graft for a given patient is that the length of the aorta is not the same for all patients and, even for the same patient the aorta has an inner diameter at the upper or proximal aortic neck and the iliac arteries have a smaller different diameter. Furthermore, the ratio between the aortic diameter and the iliac diameters are not always the same, therefore it is today necessary to have large number of grafts combining a large number of upper diameters, for the aortic neck, and lower diameters, for the iliac arteries.

The problem of the different sizes and shapes of the aortas is also an important issue at the time of placing the upper end of the graft in the correct site at the aortic proximal neck for obtaining a firm attachment of the graft on the neck and for sealing the graft against the neck of the aorta to avoid any blood flowing by the graft to leak out of the graft into the excluded aneurysm. That is, the blood flow must only circulate restricted to the interior of the graft without any leaking being produced at the attachment site. The graft includes, at each end thereof, an anchoring means, called stents, each stent being firmly attached to each graft end with a portion of each stent protruding beyond the associated end, such protruding portion being designed to be anchored against the aortic or iliac walls. Therefore, if the graft is not long enough, it may be that the stent remains firmly attached to the aortic proximal neck without the end of the graft material being correctly placed and sealed against the aortic neck wall. In this situation, the graft will be firmly retained against the aorta wall but the graft material will not be sealed against the aortic neck at the attachment site. Is not a question, however, of replacing the short graft by a longer graft to solve this problem because an extremely long graft, although covering the entire extension between the upper neck of the aorta and the corresponding iliac arteries, may have an exceeding length that becomes folded within the aorta, forming restricted zones and obstructions to the normal flow of the blood inside the graft.

Another question is that the diameter of the aortic neck must be carefully taken into account at the time of selecting the graft. If the graft is of a diameter insufficient to match the aortic neck diameter, there will be a blood leak trough a gap formed between the graft and the aortic wall. If the graft diameter is in excess, the upper edge of the graft will be folded, forming little gaps against the aortic wall, with the same leakage problems above explained. This problem is somewhat overcome by grafts made of resilient fabric, with stents made of resilient self-expanding material capable of self-expanding to a maximum diameter, or rigid stents made of a material construction that may be deformed by an expandable balloon and keep a final deformed diameter. However, the use of resilient stents are not recommended because the exceeding diameter thereof causes the aortic wall to be permanently subject to an expanding force affecting the aortic wall integrity. The use of rigid stents, although recommendable for the patient's safety, involves some installation problems as below explained.

Another problem to be taken into account when inserting and implanting a graft inside an aorta is that the graft is loaded in a multiple folded condition inside a tubular inserting or positioning device, also called introducer or sheath, a catheter for example, to carry the graft to the site of installation and to deploy the graft by radially expanding the same by any known technique, by an expandable balloon for example. To be firmly retained in the aortic proximal neck and in the corresponding iliac artery, the graft is provided at respective upper and lower ends thereof with anchoring means, as explained above, generally comprised of metal stents capable of firmly attaching the graft against the corresponding vessel wall when the stent is in the expanded condition. During the expansion, however, the upper end of the graft undergoes a rotary movement relative to the lower end of the graft. In addition, the same effect may occur in connection to the lower ends relative to the upper end of the graft. This causes the graft to be implanted with its body twisted and the flow passage defined by the graft being unduly restricted, forming a blockage to the blood flow. The rotation of the graft ends may be produced by the inflation of the balloon which is made of an inelastic material that is multiply folded in the positioning device and, upon inflation, it rotates during deployment. This rotation is transferred to the graft. The rotation induced on the graft may be also produced by the movements of the introducer into the vessel during the deployment and installation of the graft. This twisting effect appears in all grafts, either monoiliac grafts made of a cylindrical material or bi-iliac grafts, that is the bifurcated grafts.

Generally, the conventional grafts, either monoiliac and bi-iliac ones, are made of a fabric material, either of elastic knitted material or inelastic woven material. Although the elastic grafts may accommodate better the several ratios between the different diameters of the aortic neck and the iliac arteries, these grafts are dramatically affected by the problem related to the length of the graft and the twisting effect above disclosed. The grafts made of inelastic woven material are affected by all of the above mentioned drawbacks of the conventional aortic grafts.

In order to at least diminishing the above drawbacks, some bifurcated aorto-iliac grafts having a leg or limb generally longer than the other, have been developed. Thus, the shorter limb is folded within the longest limb inside the catheter and the graft is carried into the aorta. At the appropriate point when the blood flow begins to enter the graft, the shorter leg floats free in the blood stream and it is supposed to be easily directed to the proper position. However, once the upper end of this bifurcated graft is attached to the upper neck of the aorta and the lower end of the longest limb is attached inside the iliac artery through which the aorta has been acceded, the graft frequently results twisted along the upper trunk portion of the one-piece graft and the longest limb. To make the situation worst, the rotation of the trunk portion may have left the free short limb in a position diametrically opposite to the iliac artery that is free to receive said shorter limb. In this position, the longest limb, already attached inside the corresponding artery is interfering the path between the shorter limb and the free artery, thus blocking the path and preventing the shorter limb from being directed to and inserted into the corresponding free iliac artery. Therefore, although the shorter limb may have been not affected by the twisting effect, it is directed to a position that makes impossible to introduce the same into the artery.

While other monoiliac grafts and bifurcated grafts both made of several parts have been also developed, the same have been devised to form resilient-wire structures forming a helical like-spring configuration with an outer synthetic lining. These grafts, however, have a very rigid behavior which causes the same to be practically impossible to be passed through some tortuous blood vessels to reach the aorta and even practically impossible to be properly fixed in the aorta. U.S. Pat. No. 5,609,627 to Goicoechea et al. discloses a bifurcated prosthesis comprised by a wire skeleton constructed in several parts, made of nitinol wire and lined by a fabric graft layer. The nitinol wire, although flexible in a cold state, behaves like a steel wire under the temperature inside a patient's body. As it is also disclosed in this patent, Goicochea also proposes a method to install this graft consisting in placing a first bifurcated part and then enter this part by lower ends of same to introduce additional leg grafts and connect the same to lower openings in the bifurcated part. The risk of puncturing the aorta wall with the guide wire and introducer during this operation is enormous and the task of connecting the several parts inside the aorta is extremely difficult because the bifurcated part is semi-rigid and may adopt any aleatory position that causes the openings of same difficult to be reached.

U.S. Pat. No. 5,628,788 to Pinchuk et al; U.S. Pat. No. 5,632,772 to Alcime et al. and U.S. Pat. No. 5,639,278 to Dereume et al. disclose endoluminal grafts which are both expandable and supportive and are comprised of a supportive stent made of resilient wire elements and cover or liner made of a porous material over or inside the supportive wire structure. The same above explained problems are found in these grafts when trying to fold the same in an introducer, when passing the introducer through tortuous or restricted blood vessels and when fixing the stent to the available aorta wall.

Briefly, when a support-liner composite graft is tried to be accommodated inside a tortuous aorta and, because of this rigidity, the graft does not seat and seal appropriately against the aortic neck as long as the body of the graft is forced through the tortuous aortic lumen and the graft tends to adopt a straight configuration without copying the tortuous or curved aortic lumen. It is very common that this kind of grafts remain fixed in the aortic neck in an inclined configuration because when all the guide wires and introducers are removed from the aorta once the graft has been installed therein, the aorta comes back to its original tortuous configuration. Since the graft can not be accommodated to this configuration, the forces exerted by the aorta to recover its initial position is transferred directly to the graft causing the same to alter its initial connection in the aortic neck. The same alterations occur in the graft legs connected to the main graft portion and the iliac arteries. In addition to the foregoing, it also well known that the aortic neck is not always horizontal and it can be inclined as to the vertical axis of a patient's body. Under these circumstances a wire-made graft like the ones disclosed above can not be accommodated to this inclination. A similar problem is faced when the inner wall of the aortic neck is not entirely circular but has calciferous formations that make the neck inner wall irregular. this irregular perimeter can not be "copied" by a wire made graft, thus leaving portions of the aortic wall without being sealed therefore resulting in leaking of the blood flow. If, to overcome any of these problems relate to irregularities of the aortic neck, the graft is placed in a higher position, upwardly beyond the renal arteries, the flow through these arteries is blocked by the graft supportive construction formed by a dense wire mesh.

Another question related to the use of grafts made from compliant or elastic material is that the connection between the parts conforming the graft is somewhat difficult to be achieved in a safety manner as long as the compliance and elasticity of the connecting materials cause the connection to be easily released if not firmly performed. Thus, this connection requires that barbs, hooks, clips, etc. be used to firmly fix the involved parts without the risk of detaching under the effect of the blood flow and other involved forces. This problem is not found in grafts made of no-compliant or inelastic fabrics because any conventional expandable stent used to make the connection will be expanded against the maximum diameter of the connecting parts exerting an important retaining radial force.

It would be therefore convenient to have an aortic bifurcated graft capable of adapting to all of the size and shape characteristics of most of the aortas. It would also be necessary to find a new aortic graft capable of being installed without undergoing the above mentioned twisting effect and misplacing.

SUMMARY OF THE INVENTION

It is therefore one object of the present invention to provide an aortic graft and method for treatment of abdominal aortic aneurysms by inserting the graft into the aorta and into at least one iliac artery, in a way to exclude the aneurysm from the blood circulatory system, the graft comprising a two-portion or three portion tubular hollow compliant fabric material capable of accommodating any twisting and folding effect appearing in the graft as a result of the installation of the graft, that is the graft is capable of untwisting and unfolding to get its own tubular configuration after installation. The new graft is also capable of accommodating to any varying ratio between the diameters of an aortic neck and the iliac artery, the graft being also adapted to different aorta lengths and sizes, thus diminishing and even avoiding the risks of misplacing the graft inside the aorta.

It is a further object of the present invention to provide an aortic graft for treatment of abdominal aortic aneurysms, the graft comprising a tubular hollow material to be intraluminally inserted in the aorta, the aorta having an upper proximal aortic neck and a distal aortic lower portion forming an iliac bifurcation dividing into two iliac arteries, the graft comprising a graft main portion having a generally cylindrical shape with an upper end to be securely attached to the aortic proximal neck, and at least one lower end hanging, moving or floating free at a position inside the aneurysm an above the iliac bifurcation, and at least one graft iliac leg portion having a generally elongated cylindrical shape with a lower end to be securely attached to one of the iliac arteries, and an upper end to be securely connected in fluid flow communication to the lower end of the graft main portion, both graft portions being made of a flexible compliant fabric material.

It is even another object of the present invention to provide a method of treating abdominal aortic aneurysms with the graft of the invention as disclosed in the present application, the method comprising the steps of inserting a guide wire in a blood vessel at a site remote to the site of an aorta affected by the aneurysm and moving the guide wire to make it enter the aneurysm by the aortic upper neck, inserting the graft main portion over the guide wire by means of a positioning device entering the aneurysm by an iliac artery, the positioning device including at least one expandable balloon, with the graft main portion being maintained in a compressed condition inside the positioning device with least the upper end of the graft main portion located over the balloon, positioning the graft inside the aorta at the site of the aneurysm and deploying the graft main portion by inflating the balloon, whereby the upper end of the graft main portion is securely attached to the proximal upper aortic neck, downwardly removing the positioning device, permitting the lower end of the graft main portion to freely rotate relative to the upper end of the graft main portion to unfold/untwist and accommodate any rotation of the upper end generated during deploying and installation of the main graft, whereby the lower end remains in a floating or moving free relaxed condition after the upper end of the main portion has been attached to the aorta, and introducing the same positioning device or a new positioning device over the guide wire, the positioning device carrying at least one balloon and the graft leg portion in a compressed condition with at least the upper end of the graft leg portion over the balloon of the positioning device, and deploying the graft leg portion by inflating at least one balloon when the upper end of the graft leg portion is inside the lower end of the graft main portion and the lower end of the leg portion is inside a corresponding iliac artery, whereby the ends of the graft leg portion are radially expanded and securely attached against the lower end of the graft main portion and the corresponding iliac artery, with the graft main and leg portions being connected in fluid flow communication.

It is a further object of the invention to provide a method for intraluminally positioning and implanting an aortic graft according to the invention, as disclosed in the present application, the method comprising the steps of acceding to an aorta through any blood vessel connected to the aorta, preferably an iliac artery, wherein the graft is implanted by first placing a main portion of the graft against an upper proximal aortic neck and then installing a secondary leg portion in the corresponding iliac artery and connecting the main and leg graft portions to each other inside the aorta, whereby the leg portion is attached to the iliac artery and to the main portion once any rotation of the main portion, produced by the deployment and installation of the main portion, has already occurred, whereby no rotation or twisting of the graft main portion is transferred to the graft leg portion.

It is still another object of the invention to provide a method of treating abdominal aortic aneurysms with the graft of the invention, as disclosed in the application, with self-expanding anchoring means or stents, the method comprising the steps of inserting a guide wire in a blood vessel at a site remote to the site of an aorta affected by the aneurysm and moving the guide wire to make it enter the aneurysm by the upper aortic neck, inserting the graft main portion over the guide wire by means of a positioning device entering the aneurysm by an iliac artery, the positioning device including the graft main portion and a self-expanding anchoring means maintained in a compressed condition inside the positioning device, positioning the graft main portion inside the aorta at the site of the aneurysm and deploying the graft main portion by permitting the expandable anchoring means to freely expand, whereby the upper end of the graft main portion is securely attached to the proximal aortic neck while the lower end of the graft main portion remains free to rotate, downwardly removing the positioning device, permitting the lower end of the graft main portion to rotate relative to the upper end of the graft main portion, to accommodate any rotation of the main portion generated during deployment and installation thereof, whereby the lower end of the main portion remains in a relaxed condition after the upper end of the main portion has been attached to the aorta, and introducing the same positioning device or a new positioning device over the guide wire, the positioning device being inserted by the iliac artery and carrying the graft leg portion with associated self-expanding anchoring means in a compressed condition, and deploying the graft leg portion by permitting the anchoring means to freely expand when the upper end of the graft leg portion is inside the lower end of the graft main portion and the lower end of the leg portion is inside the iliac artery, whereby the ends of the graft leg portion are radially expanded and securely attached against the lower end of the graft main portion and the iliac artery, with the graft main and leg portions being connected in fluid flow communication.

It is therefore one object of the present invention to provide an aortic bifurcated graft and method for treatment of abdominal aortic aneurysms by inserting the bifurcated graft into the aorta and the iliac arteries, in a way to exclude the aneurysm from the blood circulatory system, the graft comprising a three-portion tubular hollow flexible fabric material, the material being at least partially elastic or inelastic and the graft being capable of accommodating any varying ratio between the diameters of an aortic neck and the iliac arteries, the graft being also adapted to different aorta lengths and sizes, thus diminishing and even avoiding the risks of misplacing the graft inside the aorta.

It is still another object of the present invention to provide an aortic monoiliac or bi-iliac bifurcated flexible fabric-made graft that may be implanted in an easy way without the graft undergoing the known twisting effect when being deployed against the inner wall of the aorta, thus preventing the monoiliac or the bifurcated graft from being installed in an undesired orientation.

It is a further object of the present invention to provide an aortic bifurcated graft for treatment of abdominal aortic aneurysms, the graft comprising a tubular hollow material to be intraluminally inserted in the aorta, the aorta having an upper proximal aortic neck and a lower distal portion defining an aortic bifurcation dividing into two iliac arteries, the graft comprising a graft trunk portion made of a flexible fabric material, the portion having a generally cylindrical shape with an upper end to be securely attached to the aortic proximal neck, and a lower bifurcated short portion forming two lower side-by-side connecting ends, the connecting ends extending inside the aorta and being located upwardly and spaced apart from the aortic bifurcation, and a pair of graft iliac leg portions made of a flexible fabric material, each portion having a generally elongated cylindrical shape with a lower end to be securely attached to one of the iliac arteries, and an upper end to be securely connected in fluid flow communication to a respective one of the lower connecting ends of the lower bifurcated portion of the trunk portion.

It is even another object of the present invention to provide an aortic bifurcated graft for treatment of abdominal aortic aneurysms, the graft comprising a tubular hollow material to be intraluminally inserted in the aorta, the aorta having an upper proximal aortic neck and a lower distal portion dividing into two iliac arteries, forming an iliac bifurcation, the graft comprising a graft trunk portion having a generally cylindrical shape with an upper end to be securely attached to the aortic proximal neck, and a lower bifurcated short portion forming two lower side-by-side connecting ends, at least the upper end of the trunk portion being made of a flexible elastic, radially expandable, knitted fabric material, the connecting ends extending inside the aorta and being located upwardly and spaced apart from the iliac bifurcation, and a pair of graft iliac leg portions made of a flexible elastic, radially expandable, knitted fabric material, each portion having a generally elongated cylindrical shape with a lower end to be securely attached to one of the iliac arteries, and an upper end to be securely connected in fluid flow communication to a respective one of the lower connecting ends of the lower bifurcated portion of the trunk portion.

It is a further object of the invention to provide a method of treating abdominal aortic aneurysms with the bi-iliac graft of the invention, as described and illustrated in the present specification, the method comprising the steps of inserting a guide wire in a blood vessel at a site remote to the site of an aorta affected by the aneurysm and moving the guide wire to enter the aneurysm by the upper aortic neck, inserting the graft trunk portion over the guide wire by means of a trunk-positioning device entering the aneurysm by an iliac artery and including at least one expandable balloon, with the graft trunk portion being maintained in a compressed condition inside the positioning device with at least the upper end of the graft trunk portion located over the balloon, positioning the graft trunk portion inside the aorta at the site of the aneurysm and deploying the graft trunk portion by inflating the balloon, whereby the upper end of the graft trunk portion is securely attached to the proximal aortic neck while the lower connecting ends of the graft trunk portion remain inside the aorta and above the aortic bifurcation, downwardly removing the trunk-positioning device and upwardly moving the guide wire inside the installed graft trunk portion and above the connecting ends, permitting the lower connecting ends of the graft trunk portion to follow any rotation of the upper end of the graft trunk portion generated by the balloon during inflation thereof, whereby the lower connecting ends remain in a free moving or floating relaxed condition after the upper end of the trunk portion has been attached to the aorta, without the trunk portion being affected by any twisting effect, introducing the guide wire through one of the connecting ends and making the guide wire enter one of the iliac arteries, introducing a leg-positioning device over the guide wire passing through the one connecting end of the trunk portion and the one iliac artery, the leg-positioning device carrying at least one balloon and one graft leg portion in a compressed condition with the upper end of the graft leg portion over the balloon of the leg-positioning device, and deploying the graft leg portion by inflating the balloon when the upper end of the graft leg portion is inside the one lower connecting end of the graft trunk portion and the lower end of the leg portion is inside the one iliac artery, whereby at least the upper end of the graft leg portion is radially expanded and securely attached against the one lower connecting end of the graft main portion and the iliac artery, with the graft trunk and leg portions being connected in fluid flow communication, downwardly removing the leg-positioning device and upwardly removing the guide wire, introducing a guide wire through the upper end of the installed trunk portion and make the guide wire pass through the other of the connecting ends and enter the other of the iliac arteries, introducing another leg-positioning device over the guide wire passing through the other connecting end and the other iliac artery, the another leg-positioning device carrying another graft leg portion in a compressed condition with at least the upper end of the graft leg portion over the balloon of the another leg-positioning device, and deploying the graft leg portion by inflating the balloon when the upper end of the graft leg portion is inside the other lower connecting end of the graft trunk portion and the lower end of the leg portion is inside the other iliac artery, whereby at least the upper end of the graft leg portion are radially expanded and securely attached against the other lower connecting end of the graft trunk portion and the other iliac artery, with the graft trunk portion and the other leg portion being connected in fluid flow communication, and downwardly removing the positioning device and upwardly removing the guide wire.

It is still a further object of the invention to provide a method of treating abdominal aortic aneurysms with the graft of the invention, as described and illustrated in the present specification and drawings, the method comprising the steps of inserting a guide wire in a blood vessel at a site remote to the site of an aorta affected by the aneurysm and moving the guide wire to enter the aneurysm by the upper aortic neck, inserting the graft trunk portion over the guide wire by means of a trunk-positioning device entering the aneurysm by an iliac artery and including at least one expandable balloon, with the graft trunk portion being maintained in a compressed condition inside the trunk-positioning device with at least the upper end of the graft trunk portion located over the balloon, positioning the graft trunk portion inside the aorta at the site of the aneurysm and deploying the graft trunk portion by inflating the balloon, whereby the upper end of the graft trunk portion is securely attached to the proximal aortic neck while the lower connecting ends of the graft trunk portion remain inside the aorta and above the aortic bifurcation, downwardly removing the trunk-positioning device and upwardly moving the guide wire within the installed graft trunk portion and above the connecting ends, permitting the lower connecting ends of the graft trunk portion to rotate, following any rotation of the upper end of the graft trunk portion, generated during the inflation of the balloon, whereby the lower connecting ends remain in a free moving/floating relaxed condition after the upper end of the trunk portion has been attached to the aorta, without the trunk portion being affected by any twisting effect, introducing the guide wire through one of the connecting ends and making the guide wire enter one of the iliac arteries, introducing a leg-positioning device over the guide wire passing through the one connecting end and the one iliac artery, the leg-positioning device carrying at least one balloon and a graft leg portion in a compressed condition with at least the upper end of the graft leg portion over the balloon of the leg-positioning device, moving the guide wire out of the positioning device and above the connecting ends and simultaneously placing a new guide wire inserted into the leg-positioning device through a rear end of the leg-positioning device, while the leg-positioning device remains inside the trunk portion, downwardly moving the guide wire through the upper end of the installed trunk portion and making the guide wire pass through the other of the connecting ends and enter the other of the iliac arteries, introducing another leg-positioning device over the guide wire passing through the other connecting end and the other iliac artery, the another leg-positioning device carrying at least one balloon and another graft leg portion in a compressed condition with at least the upper end of the graft leg portion over the balloon of the positioning device, deploying the graft leg portions by inflating the balloons when the upper ends of the graft leg portions are inside the corresponding lower connecting ends of the graft trunk portion and the lower ends of the leg portions are inside the iliac arteries, whereby at least the upper end of the graft leg portions are radially expanded and securely attached against the lower connecting ends of the graft trunk portion, with the graft trunk portion and the leg portions being connected in fluid flow communication, and downwardly removing the leg-positioning devices and the new guide wire, while the guide wire is upwardly removed.

It is a further object of the invention to provide a method for intraluminally positioning and implanting an aortic bifurcated graft according to the invention, as illustrated and described in the present application, by acceding to an aorta through a blood vessel, preferably a femoral artery, wherein the bifurcated graft is implanted by first placing a main trunk portion of the graft against an upper proximal aortic neck and then installing two leg portions in corresponding iliac arteries and connecting the main trunk portion to the leg portions, the trunk and leg portions being installed by inflating respective balloons to expand the portions, whereby each leg portion is attached to the trunk portion once any rotation and twisting of the trunk portion, produced by inflation of the balloon during the deployment and installation of the trunk portion, had already disappeared, whereby no rotation or twisting of the graft trunk portion is transferred to the graft leg portions.

It is still another object of the invention to provide a method of treating abdominal aortic aneurysms with the graft of the invention, as disclosed and depicted in the present application and drawings, the method comprising the steps of inserting a guide wire in a blood vessel at a site remote to the site of an aorta affected by the aneurysm and moving the guide wire to enter the aneurysm by the upper aortic neck, inserting the graft trunk portion over the guide wire by means of a trunk-positioning device with the graft trunk portion and associated self-expanding anchoring means being maintained in a compressed condition inside the trunk-positioning device, positioning the graft trunk portion inside the aorta at the site of the aneurysm and deploying the graft trunk portion by permitting the anchoring means to radially expand, whereby the upper end of the graft trunk portion is securely attached to the proximal aortic neck while the lower connecting ends of the graft trunk portion remain inside the aorta and at a position above the aortic bifurcation, downwardly removing the trunk-positioning device and upwardly moving the guide wire within the installed graft trunk portion and above the connecting ends, permitting the lower connecting ends of the graft trunk portion to follow any rotation of the upper end of the graft trunk portion, generated by the expansion of the anchoring means, whereby the lower connecting ends remain in a relaxed condition after the upper end of the trunk portion has been attached to the aorta, introducing the guide wire through one of the connecting ends and making the guide wire enter one of the iliac arteries, introducing a leg-positioning device over the guide wire passing through the one connecting end and the one iliac artery, the leg-positioning device carrying one graft leg portion with associated self-expanding anchoring means in a compressed condition, moving the guide wire out of the positioning device and above the connecting ends and simultaneously placing a new guide wire inserted into the leg-positioning device through a rear end of the leg-positioning device, while the leg-positioning device remains inside the trunk portion, downwardly moving the guide wire through the upper end of the installed trunk portion and make the guide wire pass through the other of the connecting ends and enter the other of the iliac arteries, introducing another leg-positioning device over the guide wire passing through the other connecting end and the other iliac artery, the another leg-positioning device carrying another graft leg portion with associated self-expanding anchoring means in a compressed condition, deploying the graft leg portions by permitting the expandable anchoring means to freely expand the upper ends of the graft leg portions when they are inside the lower connecting ends of the graft trunk portion and the lower ends of the leg portions are inside the iliac arteries, whereby at least the upper end of the graft leg portions are radially expanded and securely attached against the lower connecting ends of the graft main portion, with the graft trunk portion and the leg portions being connected in fluid flow communication, and downwardly removing the leg-positioning devices and the new guide wire, while the guide wire is upwardly removed.

It is still a further object of the invention to provide an aortic graft for treatment of abdominal aortic aneurysms, the graft comprising a tubular hollow material, either of the monoiliac type or the bi-iliac type, to be intraluminally inserted in the aorta, the aorta having an upper proximal aortic neck and a distal aortic lower portion forming an iliac bifurcation dividing into two iliac arteries, the graft comprising a graft main portion having an upper end to be securely attached to the aortic proximal neck, and a lower end hanging free at a position inside the aneurysm an above the iliac bifurcation, and a graft iliac leg portion having a generally elongated cylindrical shape with a lower end to be securely attached to one of the iliac arteries, and an upper end to be securely connected in fluid flow communication to the lower end of the graft main portion, both graft portions being made of a compliant, elastic knitted material, and the main portion being downwardly tapered towards the end thereof, the end of the main portion terminating in an inelastic edge, whereby the upper end of the leg portion may be retained within the tapered lower portion by anchoring means, with the inelastic edge encircling the upper end of the graft leg portion and the anchoring means remaining within the graft main portion upwardly of the inelastic edge.

It is still another object of the invention to provide a bi-iliac bifurcated graft as defined above and assembling a pair of pants with two pending legs, the graft being capable of being converted into a monoiliac type graft by means of simple modification, the graft comprising a main upper portion and a leg portion to be connected to the main portion, the graft being made of a compliant elastic knitted material and the main portion including a lower inelastic edge formed by an inelastic thread passing through the elastic knitted material of the graft main portion at a lower edge of one of the legs of the pants, an additional inelastic thread passing through the knitted material in the other leg at a point of bifurcation of the two pending legs of the pants, whereby the other pending leg of the pants may be closed to the blood flow to convert the bifurcated graft into a monoiliac aortic graft.

It is a further object of the invention to provide a method for treating abdominal aortic aneurysms by installing inside the aorta graft as disclosed above, the method comprising the steps of placing the main graft portion inside the aorta whereby the portion is firmly retained against the upper aortic neck with a lower edge of the graft main portion freely moving inside the aneurysm, inserting the upper end of the leg portion inside the lower portion of the main graft portion, and expanding the anchoring means of the leg portion once the anchoring means are at least partially inside the lower portion of the graft main portion, whereby the anchoring means defining, in the expanded condition, and in at least a section thereof upwardly the inelastic edge, a maximum diameter larger than the predetermined maximum diameter of the inelastic edge, whereby the upper end of the leg portion may be retained within the lower portion of the main portion by the anchoring means, with the inelastic edge encircling the upper end of the graft leg portion and the anchoring means remaining, at least partially, within the graft main portion upwardly of the inelastic edge.

It is yet another object of the invention to provide a method for treating abdominal aortic aneurysms by installing inside the aorta the graft of the invention, the method comprising the steps of making a knot in free ends of the thread passing through the knitted material at the lower inelastic edge to define a predetermined maximum diameter of the inelastic edge, placing the main graft portion inside the aorta whereby the portion is firmly retained against the upper aortic neck with a lower edge of the graft main portion freely moving inside the aneurysm, inserting the upper end of the leg portion inside the lower portion of the main graft portion, and expanding the anchoring means of the leg portion once the anchoring means are at least partially inside the lower portion of the graft main portion, whereby the anchoring means defining, in the expanded condition and in at least a section thereof upwardly the thread knotted in the lower inelastic edge, a maximum diameter larger than the predetermined maximum diameter of the inelastic edge, whereby the upper end of the leg portion may be retained within the lower portion of the main portion by the anchoring means, with the inelastic edge encircling the upper end of the graft leg portion and the anchoring means remaining, at least partially, within the graft main portion upwardly of the inelastic edge.

To the purpose of this invention the term "flexible fabric" should be understood as any textile material or fabric of surgical grade, biocompatible, capable of being flexed in such a way that the tubular graft portions of the invention can follow the curved path of any vessel, even tortuous vessels, to accede to the aorta, and even capable of being accommodated into the aorta when the aorta has a multiply curved path, without any strangulation appearing in the tubular shapes of the graft portions, and without affecting the attachment at the respective ends of the portions and the aorta and iliac arteries.

When the term "pending" or "hanging" is used associated to some portions of the graft of the invention, it is attempted to mean that such portions, like the ends or the end portions of the main/trunk portions remain free and capable of freely moving, rotating, waving, floating, etc., in the blood flow, for example. These terms have been used to illustrate the capability of the main/trunk portion to accommodate to the aorta configuration and blood flow, and the terms were elected to make more illustrative this behavior of the graft in the position it is shown in the Figures, that is in a vertical position. However, in any surgical operation, the patient is horizontally positioned, whereby the main/trunk graft portion of the inventive embodiments will be freely moved by the blood flow in an horizontal pattern. Therefore, the terms pending and hanging, when used for the main/trunk portion once attached to the upper aortic neck, must be understood according to this explained concept.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 9 shows a side elevation, partial cross-sectional view of the aorta and graft trunk portion of FIGS. 7, 8, with two leg-positioning devices each inserted through respective right and left iliac arteries into the aorta, both leg-positioning devices containing the respective graft leg portions ready to be installed within the aorta and the respective iliac arteries;

FIG. 10 shows a side elevation, partial cross-sectional view of the aorta, the graft trunk portion and both leg portions connected to the graft trunk portion and installed in place inside the iliac arteries;

FIG. 14 shows a side elevation, partial cross-sectional view of an aorta, with a monoiliac graft made of woven inelastic material and comprising an upper graft main portion connected to a graft lower leg portion;

FIG. 15 is an enlarged view of the portion of the connection between the main and leg portions encircled by the circle depicted in phantom lines in FIG. 14;

FIG. 16 is a side partial lateral view of a connection between a lower end of the graft main portion and an upper end of the lower graft leg portion performed according to the teachings of the invention;

FIG. 17 is an enlarged view of the inelastic edge of the main graft portion encircled in the rectangle depicted in phantom lines if FIG. 16, and FIG. 18 is an elevation view of a bifurcated trunk portion including the teachings of the invention.

DESCRIPTION OF THE PREFERRED EMBODIMENTS

Figure 1:
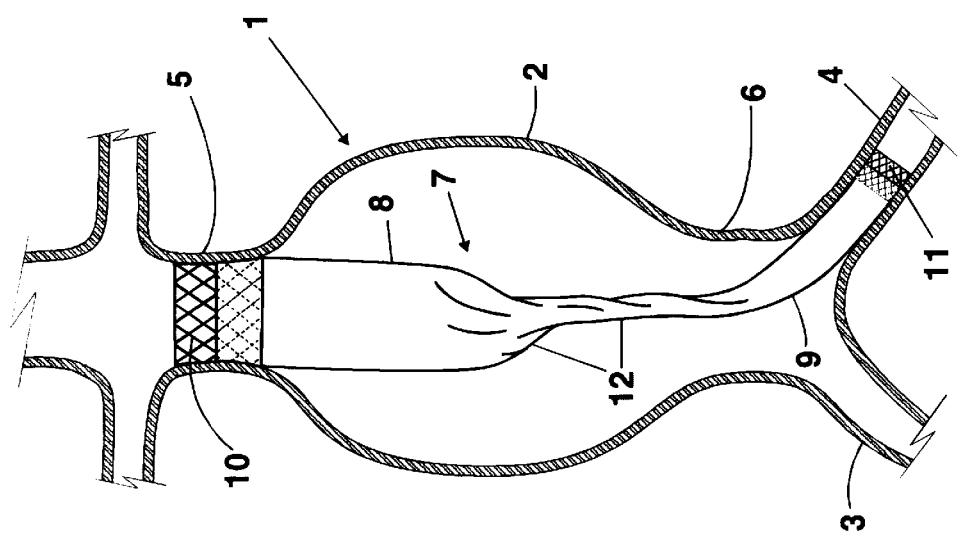
FIG. 1 shows a side elevation view of an aortic monoiliac type graft of the prior art once installed inside the aorta.

Now referring in detail to the drawings it may be seen from FIG. 1 an infra-renal aorta generally indicated by numeral reference 1, affected by an aneurysm consisting of an abnormal dilation 2 of the aortic wall. The aorta arises form the heart (not illustrated) and runs downwardly to divide into the iliac arteries 3, 4. When the aorta is affected by the aneurysm an upper proximal aortic neck 5 and a lower distal aortic neck 6 are defined at upper and lower parts of the aneurysm. It also may be that distal neck 6 is not formed, but the wall is also dilated, when the aneurysm extends to the bifurcation and also through the iliac arteries. If not treated, dilated wall, or aneurysm 2, becomes ruptured with ensuing fatal hemorrhaging in a very short time. Many attempts have been made to prevent and avoid the high mortality due to this abnormality, most of the attempts involving surgical techniques with associated high risk for the patient. In the recent years a less traumatic technique has been developed consisting of acceding the aorta intraluminally to insert and install inside the aorta a graft to exclude the aorta from the blood circulatory system. When installing the graft in the aorta the graft may be firmly attached to those portions of the aortic wall in good conditions to provide a safe attachment, that is a firm anchoring and sealing coupling between the aortic graft and the aorta.

Figure 5:
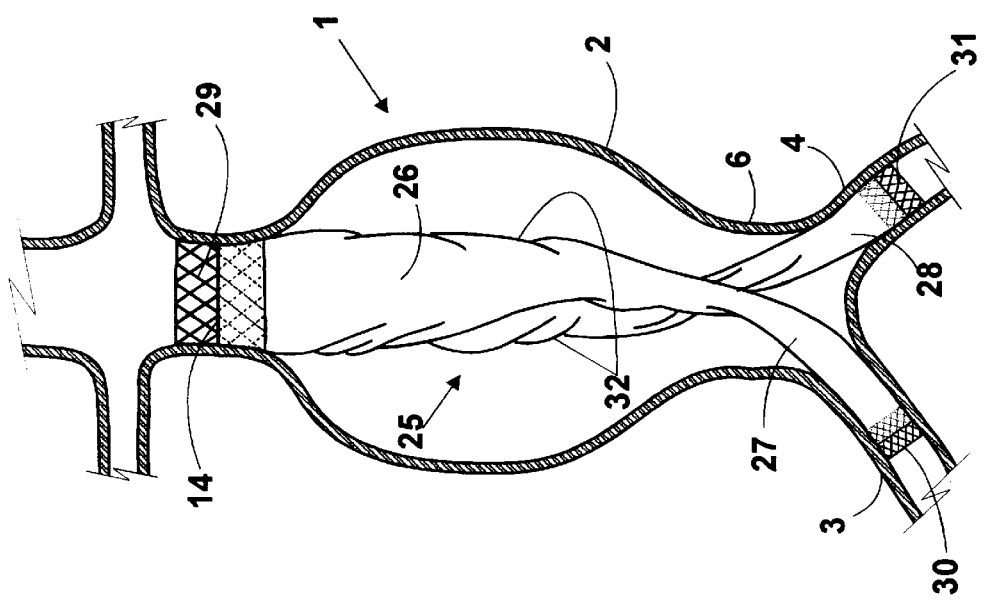
FIG. 5 shows a side elevation view of an aortic one-piece bifurcated graft of the prior art once installed inside an aorta.

Among the several aortic grafts three main graft types may be identify, namely the monoiliac aortic graft, shown in FIG. 1, comprising a cylindrical tubular one-piece or two-piece graft, the bi-iliac aortic grafts consisting of a bifurcated graft comprising an inverted Y-shape tubular graft, shown in FIG. 5, and the aorto-aortic graft (not shown) consisting of a sleeve with an upper stent to be attached to an upper neck of the aorta and a lower stent to be attached at a lower aortic neck. The aorto-aortic grafts not always can be used because it is frequent that the aneurysm has reached an extent that the lower aortic neck 6, excessively dilated, has disappeared and the lower end of the graft does not find a firm aortic wall to be fixed.

As to the bifurcated grafts, the same are designed to have the trunk of the Y inserted and firmly attached to proximal neck 5 of the aorta while each branch or leg of the Y is inserted and installed inside a respective iliac artery 3, 4. The use of bifurcated grafts, however, has shown many inconveniences as to the installation thereof, as it will be further disclosed below when referring to the bifurcated embodiment of the invention.

In view of the foregoing, the inventor of the present invention has developed a new graft, either monoiliac or bi-iliac graft that can be installed without being affected by the above and below remarked drawbacks.

Monoiliac Aortic Graft:

A monoiliac aortic graft according to the prior art is shown in FIG. 1, the graft comprising a tubular material having an upper portion 8 with a larger diameter to be attached to the aortic proximal neck and a lower portion 9 having a smaller diameter to be installed within one 4 of the iliac arteries 3, 4. The fluid communication is thus defined between the aorta and iliac artery 4, then, the blood flow in iliac artery 3 is obtained by performing a connection between arteries 3 and 4 by a simple surgery downstream of the iliac bifurcation, the surgery being carried out in a zone of the human body where no vital organs are exposed to risks and iliac artery 3 is closed to avoid any blood back flow into the aneurysm through artery 3. Although the implanting of the monoiliac graft has shown to be simpler than the installation of the bi-iliac graft, the correct positioning of the graft is still hard to be obtained in the desired manner.

As it is well known in the art, the graft must be positioned inside the aorta by means of a tubular positioning device, such as an introducer or sheath. To this purpose the graft is multiply folded and compressed to fit snugly into the tubular positioning device, the positioning device is then introduced within the blood circulatory system of a patient to accede to the aorta with the graft in the device, with predetermined anchoring portions of the graft being folded around respective expandable balloons also located inside the positioning device. Once in the desired site where the graft is to be implanted, the graft is moved out of the positioning device and the expandable balloons are inflated to expand the graft. The graft is provided with anchoring means, preferably stents 10, 11, generally consisting of a metal expandable mesh capable of being expanded and keeping its expanded configuration after the balloon is deflated. Each stent is located over a balloon, therefore, once the balloon is expanded the stent is radially outwardly deformed whereby it is firmly attached against the wall of the aorta, preferably at the proximal aortic neck, at any healthy portion of the aortic wall, or against a wall of the respective iliac artery. In FIG. 1, two stents are depicted, stent 10 is attached to aortic neck 5 while stent 11 is attached to iliac artery 4.

When graft 7 is moved out of the introducing device and the balloons are inflated the fabric material of which the graft is made is deployed with a rotary uncontrolled effect that causes the graft to be installed in a twisted configuration like the one shown in FIG. 1. With the graft twisted as illustrated, the necessary cross-section of the tubular graft is dramatically reduced and restricted, forming restriction zones 12 that affect the blood flow, and causes the patient to be treated by open surgery to remove the twisted or folded graft and insert a new conventional graft.

Figure 2:
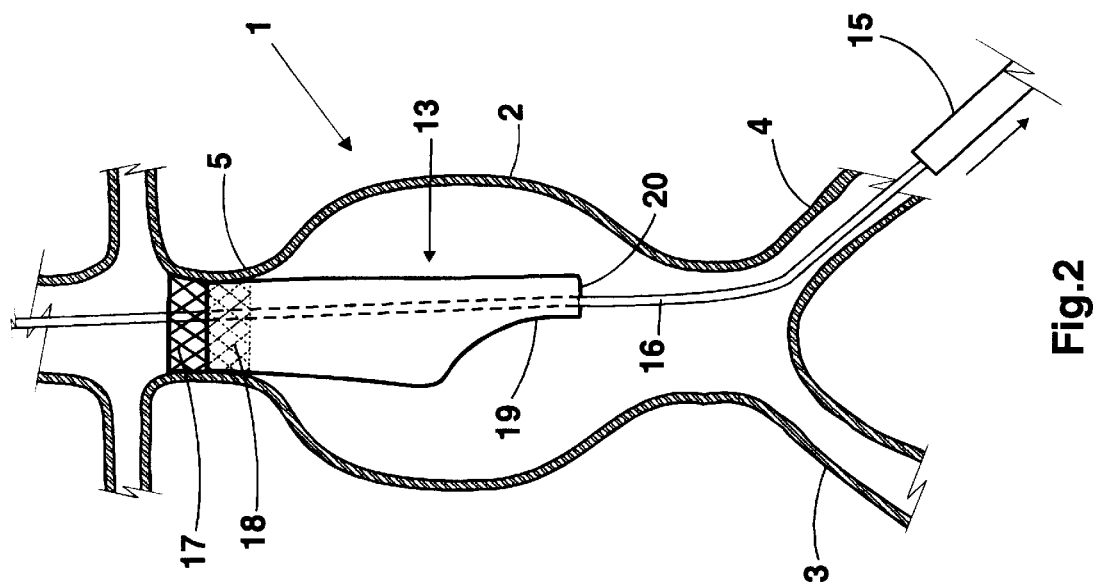
FIG. 2 shows a side elevation, partial cross-sectional view of an aorta with a graft main portion of the invention already installed inside the aorta, over a guide wire.
Figure 3:
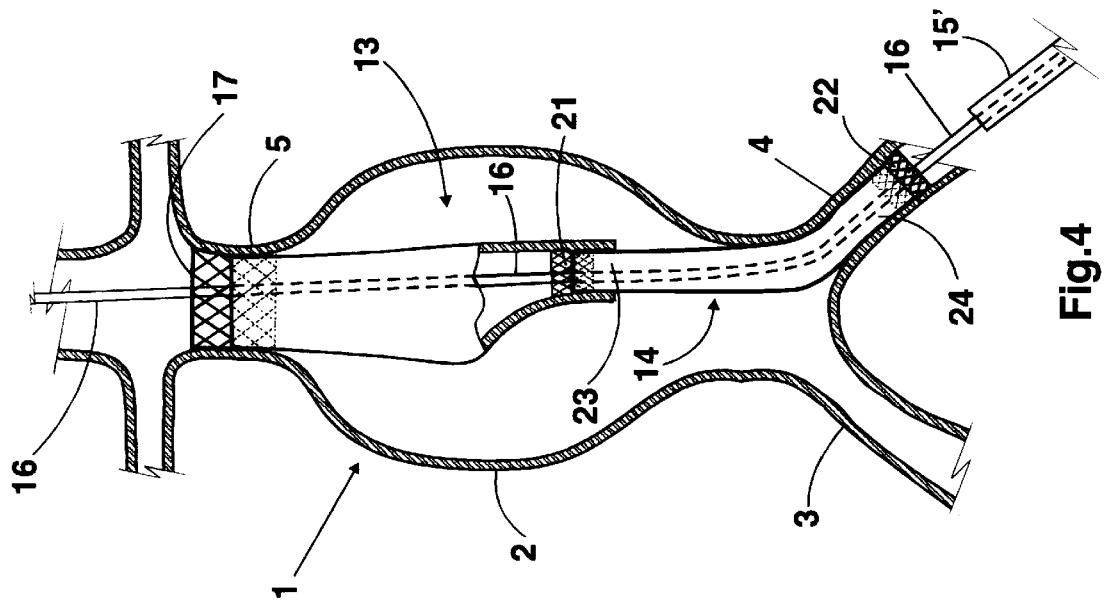
FIG. 3 shows a side elevation, partial cross-sectional view of the aorta and graft main portion of FIG. 2 with a positioning device passed through the graft main portion and ready to positioning of a graft leg portion.
Figure 4:
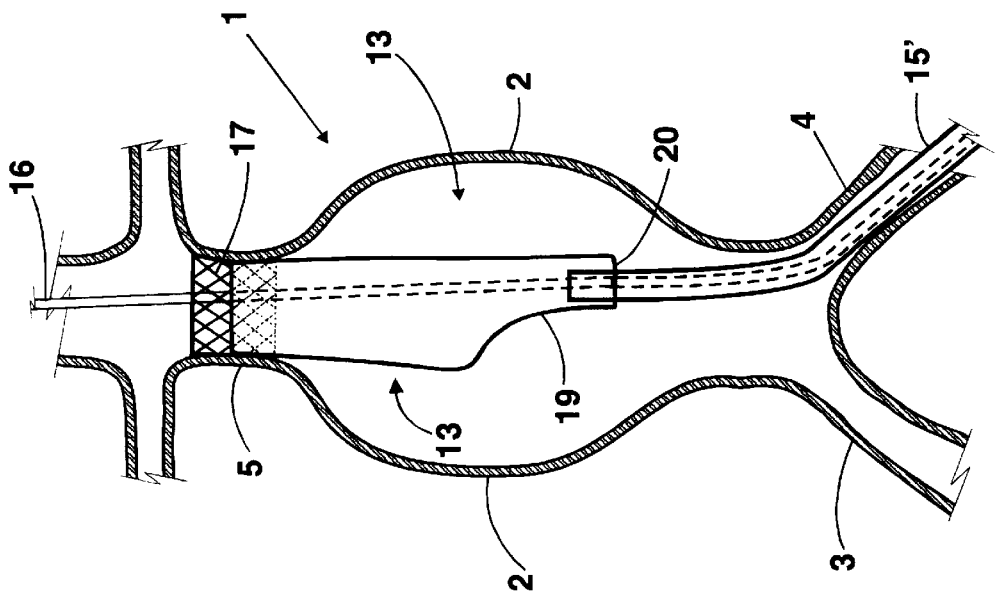
FIG. 4 shows a side elevation, partial cross-sectional view of the aorta and graft main portion of FIG. 2, with a graft leg portion connected to the graft main portion and installed in place.

According to the invention, a new aortic graft is provided, comprising a two-part graft illustrated in FIGS. 2–4. The inventive graft comprises a graft main portion 13 adapted to be attached to neck 5, and a graft leg portion 14 (FIG. 4) adapted to be attached to portion 13 and to one 4 of the iliac arteries 3, 4. Graft main portion 13 may be placed inside aorta 1 by any of the known techniques, by means of a introducer or tubular positioning device 15 running over a conventional guide wire 16.

According to the method of the invention, guide wire 16 is first inserted into the blood circulatory system and moved to reach the aorta by making an incision in a blood vessel at a site remote from the aorta. Preferably, the incision is made in the groin of the patient to enter through a femoral artery, the incision, however, may be made in any other blood vessel as long as acceding to the aorta is ensured. A positioning device 15' carrying graft portion 13 and stent 17 firmly fixed at an upper end 18 of the graft portion is inserted into the incision and fed into the aorta. The stent and the graft snugly fit into the positioning device with the stent crimped over a balloon catheter (not shown) and the graft is wrapped around the stent and the balloon catheter, as it is conventionally used in a positioning device. Once the device is in the desired position inside the aorta, particularly when stent 17 and end 18 are positioned as it is shown in FIG. 2, the balloon is inflated to radially outwardly deform the stent to cause the same to be attached against the aortic wall at neck 5, with an upper edge of end 18 sealing against neck 5 to avoid any blood leakage. To assist in the correct positioning of the graft, radio-opaque marks, or indicia, may be provided in upper end 18 and the balloon as it is well known in the art. Stent 17 may be, alternatively, of a resilient type with a tendency to expand to its relaxed condition at a fixed maximum diameter when the stent is released from its compressed condition as it is loaded inside the catheter, or, as it was above disclosed, the stent may be of the rigid type in which event the stent is made of a metallic mesh that is also loaded in a compressed condition inside the catheter but is radially outwardly deformed by the balloon into a permanent expanded condition. A rigid type stent is capable of retaining a permanent expanded deformation to firmly retain the graft against any forces from the blood flow and movements of the patient. Stent 17 is be made of any suitable biomedical grade metal.

Graft main portion 13 has a generally cylindrical shape with upper end 18 to be securely attached to aortic proximal neck 5, and a tapered lower end portion forming and end 19 that is tapered by the diameter thereof reducing towards a lower edge 20 having the smallest diameter of the graft portion. Particularly, tapered lower end 19 is a cone-shaped portion the diameter of which decreases towards edge 20. Once placed in the site, unfolded and untwisted lower end 19 and edge 20 may result positioned as it is shown in FIG. 2, or may be positioned and oriented in any other position rotated about a longitudinal axis of the graft. At either of the positions of end 19, this end will always be well unfolded, untwisted and oriented in such a way that it will be free of any flow restriction and will be aligned with the iliac artery through which the guide wire and positioning device have entered the aneurysm, in the drawing, artery 4. Even in any position rotated relative to the position shown in FIG. 2, end 19 and edge 20 will remain in a convenient orientated position relative to any of the iliac arteries. This is very important to then connect the leg portion as it will be explained below. One of the most important features of the two part-graft of the invention is that when graft portion 13 is installed by deployment of the same from the positioning device, any rotation and/or twisting effect resulting from the outwardly deployment will disappear, even if the guide wire is not removed. Graft portion 13 may accommodate itself over the guide wire in order that the rotation thereof originated during installation will not twist the material because end 19 of the invention is free to rotate by accompanying the rotation upper end 18. When accompanying rotation, end 19 will result positioned in any of the rotated positions as explained above, without any twisted zones, thus differing from the case of the one-piece graft shown in FIG. 1.

Also according to the method of the invention, the second part of the graft, leg portion 14, is inserted into the aorta and connected to main portion 13. Positioning device 15, containing the loaded folded leg portion 14 and respective stents 21, 22, is conveyed over guide wire 16, so that device 15 is inserted into graft portion 13, particularly up to the position shown in FIG. 3. Once in this position, leg portion 14 is moved out of catheter 15 and deployed, by inflating, preferably simultaneously, respective balloons at the sites of stents 21, 22, into the configuration shown in FIG. 4, thus the leg portion being firmly attached to portion 13 and to iliac artery 4. Tubular positioning device is then removed as indicated by the arrow in FIG. 4. Like stent 17, stents 21, 22 may be of a resilient type or may be of the rigid type as well as they are made of any suitable biomedical grade metal. When self-expandable stents are used no balloons may be necessary to expand the above mentioned portions of the graft. Thus, the stents are just permitted to expand.

Graft iliac leg portion 14 has a generally cylindrical shape with an upper end 23 to be securely connected in fluid flow communication to lower tapered portion or end 19 of the graft main portion, and a lower end 24 securely attached to one 4 of the iliac arteries. Graft leg portion 14 has a diameter smaller than the diameter of the graft main portion, the diameter of the graft main portion decreasing towards the lower end of the graft main portion to securely receive the upper end of the graft leg portion. End 23 being retained against end 19 by the expanded stent and end 23 of the leg portion is prevented from being dislodged because of the tapered configuration of end portion 19 forming a diameter interference in an overlapping between ends 19, 23. Any other kind of interference may be performed by a clamp or suture made at end 19, before installation, so as to restrict the diameter of end 19.

Briefly, the method according to the invention comprises acceding to the aorta through an acceding blood vessel, preferably an iliac artery, wherein the graft is implanted by first placing main portion 13 as explained and then installing the secondary leg portion in the corresponding iliac artery 4 and connecting the main and leg graft portions to each other, whereby leg portion 14 is attached to the iliac artery and to main portion 13 once any rotation of the main portion, produced by the deployment and installation of the main portion has already occurred, whereby no rotation or twisting of the graft main portion is transferred to the graft leg portion.

More particularly, the method comprises inserting guide wire 16 in a site remote to the site of the vessel affected by the aneurysm, preferably the aorta, and moving the guide wire to the site of the aneurysm; inserting the graft main portion over the guide wire by means of a positioning device, such as an introducer 15, including at least one expandable balloon, with the graft main portion being maintained in a compressed condition over the balloon; placing the graft in the site of the aneurysm and deploy the graft main portion by inflating the balloon, whereby upper end 18 of graft main portion 13 is securely attached to proximal aortic neck 5; removing the positioning or placing device and introducing the same or another new positioning device over the guide wire, the positioning device carrying the graft leg portion in a compressed condition until upper end 23 of the graft leg portion is inside lower end 19, passing edge 20, of the graft main portion, and deploying the graft leg portion by inflating the balloon of the catheter when the upper end of the graft leg portion is at the lower end portion of the graft main portion, whereby the upper end of the graft leg portion is radially expanded and securely attached against the lower end of the graft main portion, with the graft main and leg portions connected in fluid flow communication.

With the inventive graft and method of the invention the drawbacks of the conventional grafts and implanting methods are avoided, or at least minimized. Thus, the rotation generated during the installation of a prior art graft, due to the fact that both the upper and lower ends of a one-piece graft are retained at the upper neck of the aorta and the iliac artery, any rotation of the ends can not be accommodated and the graft tubular body becomes twisted as shown in FIG. 1. With the present invention, the rotation of graft 13 is accommodated as long as end 20 is free to rotate once end 18 has been retained inside neck 5, therefore the twisting effect does not occur in the tubular body of graft 13 because end 20 rotates in the same extent that end 18 has rotated. Then, leg portion 14 is installed as above explained.

Another advantage of the present invention as compared to the prior art is that the different ratios of the diameter of neck 5 and the diameter of iliac artery 3, 4, could be covered with only one main portion 13, or a few main portions, useful for any length of aorta, while the leg portion will be selected from a set of leg portions having different diameters and standard lengths. This combination of different main portions and different leg portions provides a wide spectrum of combinations that is also very helpful to cover a large number of lengths to correctly positioning of the graft along the entire distance between neck 5 and the necessary portion of the iliac artery, thus achieving a proper anchoring effect of the graft and a complete aneurysm exclusion.

Another important aspect of the invention is related to the use of anchoring means of the resilient type, that is self-expanding stents. In the prior art grafts, the twisting effect to which wide reference has been made in connection to the use of rigid stents may also appear when using resilient stents because the graft is longitudinally placed within the tubular positioner or applicator and, when the graft is left to move out from the applicator the stents are released in a no simultaneous pattern. Under these circumstances, if graft 7 of FIG. 1 is being installed stent 10 is first expanded with the usual rotation thereof while stent 11 still remains inside the positioning device, thus the rotation of stent 10 generates a twisting effect along sleeve 7 and this twisting effect may be increased by any rotation of the positioning device when moving during the removal thereof to leave stent 11 expanded in a position rotated relative to stent 10. Therefore, the fact of leaving lower end 20 of the invention to freely rotate after stent 10 has been attached to neck 5 makes the graft to accompany the rotation of the stent thus preventing the graft from remaining twisted or folded.

Bifurcated Bi-Iliac Aortic Graft:

Now referring in detail to another embodiment of the invention devised by a bifurcated graft, a bi-iliac bifurcated graft according to the prior art may be seen in FIG. 5. The known bi-iliac aortic graft consists of a bifurcated graft 25 comprising an inverted Y-shape tubular graft. The bifurcated graft is designed to have a trunk 26 of the Y inserted and firmly attached to proximal neck 5 of the aorta while each branch, limb or leg 27, 28 of the Y is inserted and installed inside a respective iliac artery 3, 4.

Although the bifurcated grafts provide for a better design that should define a complete and fluid connection between the aorta and the iliac arteries, the bifurcated grafts are affected by restrictions during the installation thereof as long as the connection of the leg portions to the trunk portion has been very complex and no reliable with the methods today available, particularly to position and deploy the graft into the aorta in a way that the graft were firmly and properly located in place. Although the trunk of the bifurcated graft could be placed in a conventional way, there were no reliable devices and techniques to position and attach the limbs of the Y in the correct place, within the respective iliac arteries.

According to the conventional grafts today available for aortic repairing, the graft must be positioned inside the aorta by means of a tubular positioning device, such as an introducer. To this purpose the graft is multiply folded and compressed to fit snugly into the tubular positioning device, the positioning device is then introduced within the blood circulatory system of a patient to accede to the aorta with the graft in the device, with predetermined anchoring portions of the graft being folded around at least one expandable balloon also located inside the positioning device. Once in the desired site where the graft is to be implanted, the graft is moved out of the positioning device and the expandable balloon or balloons is inflated to expand the graft. The bifurcated graft is provided with anchoring means, preferably stents 29, 30, 31 each generally consisting of a metal expandable mesh capable of being expanded and keeping its expanded configuration after the balloon is deflated. The stent is located over the balloon, therefore, once the balloon is expanded the stent is radially outwardly deformed whereby it is firmly attached against the wall of the aorta, at the proximal aortic neck, and against a wall of the respective iliac artery. In FIG. 5, three stents are depicted, stent 29 is attached to aortic neck 5 while stents 30 and 31 are attached to respective left and right iliac arteries 3 and 4.

When graft 25 is moved out of the introducing device and the balloons are inflated the fabric material of which the graft is made is deployed with a rotary uncontrolled effect that causes the graft to be installed in a twisted configuration like the one shown in FIG. 5. With the graft twisted as illustrated, the necessary cross-section of the tubular graft is dramatically reduced and restricted, forming restriction zones 32, this effect being made worse by the bifurcation defined between the trunk portion 26 and limbs 27, 28, which causes the blood flow to be blocked and the patient must be treated by open surgery to remove the twisted and/or folded graft and insert a new conventional graft.

According to another embodiment of the invention, a new aortic graft is provided, comprising a three-part graft illustrated in FIGS. 6–13. The inventive graft comprises a graft trunk portion 33 adapted to be attached to neck 5, and two graft leg portions 34 and 35 (FIGS. 8, 9, 11, 12) adapted to be attached to portion 33 and to the iliac arteries 3, 4. Graft trunk portion 33 may be placed inside aorta 1 by any of the known techniques, by means of an introducer or tubular trunk-positioning device 36 (FIGS. 6, 12) running over a conventional guide wire 37.

Figure 6:
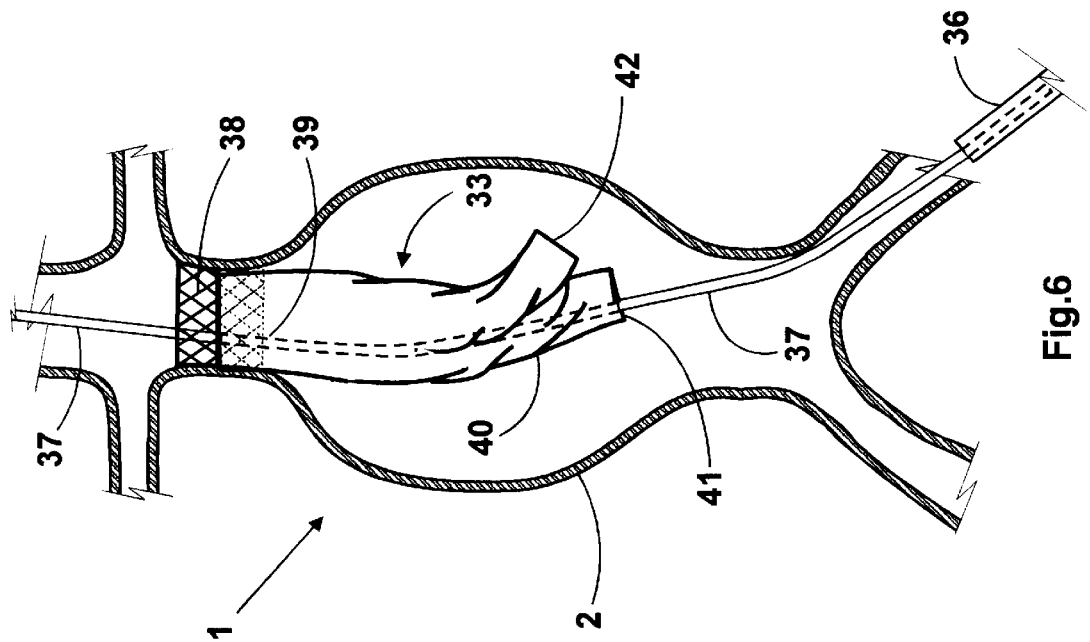
FIG. 6 shows a side elevation, partial cross-sectional view of a step of the inventive method once the trunk-positioning device is being removed with the trunk portion retained in the aortic neck, over the guide wire and twisted.

According to the invention, guide wire 37 is first inserted into the blood circulatory system and moved to reach the aorta by making an incision in a blood vessel at a site remote from the aorta. Preferably, the incision is made in an artery in one of the arms of a patient. Guide wire 37 is then conveyed to enter by aortic neck 5 and towards one of the femoral arteries through which artery the guide wire is taken out of the patient's body through an incision in the groin of the patient so that a leading end of the guide wire is thus used to introduce a trunk-positioning device over the guide wire into the femoral artery. Trunk-positioning device 36 carrying graft portion 33 and an anchoring means, such as a stent 38 firmly fixed at an upper end 39 of the graft trunk portion, is inserted into the incision and fed into the aorta. The stent and the graft snugly fit into the trunk-positioning device and the stent is placed around a balloon (not shown) as it is conventionally used in an inserting or positioning device. Once the positioning device is in the correct position inside the aorta, particularly when stent 38 and end 39 are positioned as it is shown in FIG. 6, the balloon is inflated to radially outwardly deform the stent to cause the same to be attached against the aortic wall at neck 5, with any upper edge of end 39 sealed against neck 5 to avoid any blood leakage. To assist in the correct positioning of the graft, radio-opaque marks, or indicia, may be provided in upper end 39 and the balloon as it is well known in the art. Stent 38 may be of a resilient type with a tendency to expand to its relaxed condition at a fixed maximum diameter when the stent is released from its compressed condition as it is loaded inside the introducer, or may be of the rigid type in which event the stent is made of a metallic mesh that is also loaded in a compressed condition inside the catheter but is radially outwardly deformed by the balloon into a permanent expanded condition. A rigid type stent is capable of retaining a permanent expanded deformation to firmly retain the graft against any forces from the blood flow and movements of the patient. Stent 38 is be made of any suitable biomedical grade metal. In any event, stent 38 is made of an open wire structure that, if upper aortic neck is dilated or irregular to bar a firm mounting of the stent, the stent may be placed beyond the renal arteries provided that the graft fabric do not close the arteries, and the wire stent will not block the blood flow through the renal arteries.

Graft trunk portion 33 has a generally cylindrical shape with upper end 39 to be securely attached to aortic proximal neck 5, and a lower bifurcated short portion 40 forming two lower side-by-side connecting ends, a left connecting end 41 and a right connecting end 42. This configuration of the trunk portion assemblies a pair of pants, therefore connecting ends 41 and 42 may be also referred to along this description as pending legs of the pant.

Figure 7:
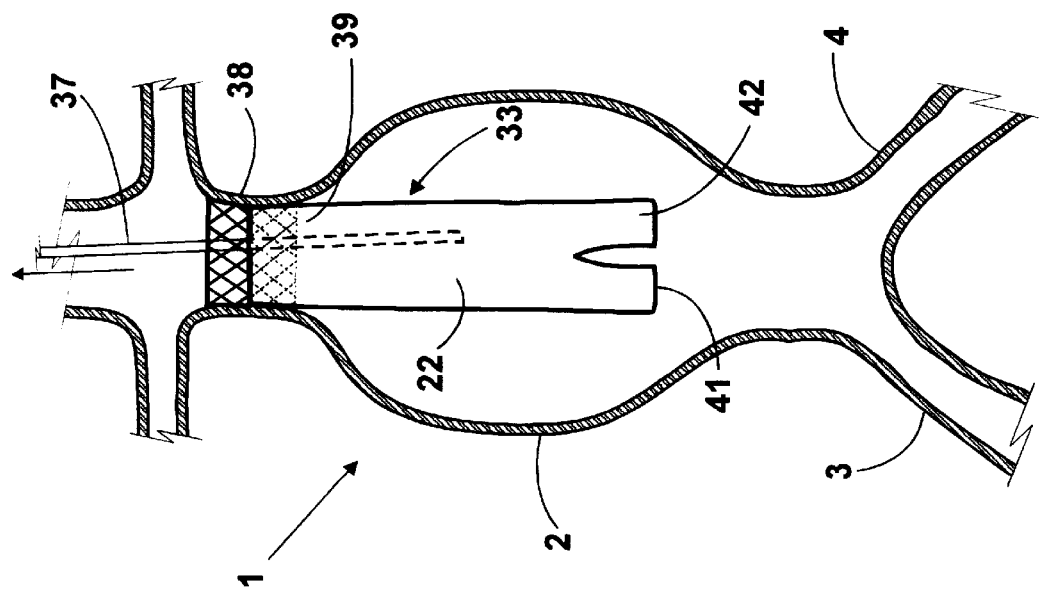
FIG. 7 shows a side elevation, partial cross-sectional view of an aorta with the graft trunk portion of FIG. 6 already installed inside the aorta, with the guide wire being upwardly removed from one end of the trunk so that the trunk portion is permitted to freely rotate inside the aorta and result positioned in the best favorable condition having the bifurcation oriented according to the iliac arteries.

Once placed in the site, lower ends 41 and 42 may result positioned as it is shown in FIG. 7, that is the most favorable position with both ends almost aligned with iliac arteries 3, 4. Otherwise, ends 41, 42 may result positioned in any other position rotated about a longitudinal axis of the graft trunk, that is a less favorable position. According to the invention, however, whatever the position of ends 41 and 42 is resulted these ends will always be unfolded untwisted and well oriented for a correct further connection to leg portions 34, 35 to iliac arteries, as will be further explained in connection to FIGS. 9–13. That is, even in a position rotated 90° relative to the position shown in FIGS. 7–10, that is in the position shown in FIGS. 11–13, ends 41, 42 will remain in a convenient orientated position relative to any of the iliac arteries. This is possible because ends 41, 42 are free moving from the trunk portion like in a pair of pants, thus permitting the ends to be moved in opposite directions without obstructing the blood flow, that is the ends or pending legs are not connected to each other like in some three-part grafts of the prior art.

One of the most important features of the three part-graft of the invention is that when graft portion 33 is installed by deployment of the same from the positioning device, any rotation and/or twisting effect resulting from the outwardly deployment will disappear by removing guide wire 37 by pulling the guide wire upwardly. Any rotation of trunk portion, originated during the installation thereof, will not twist the material because ends 41 and 42 of the invention are free to move, float or rotate to accompany the rotation of upper end 39 and will result positioned in any of the rotated positions as explained above, even in a worse position, shown in FIGS. 11–13, without any twisted zones, thus differing from the case of the one-piece bifurcated graft shown in FIG. 5.

Figure 8:
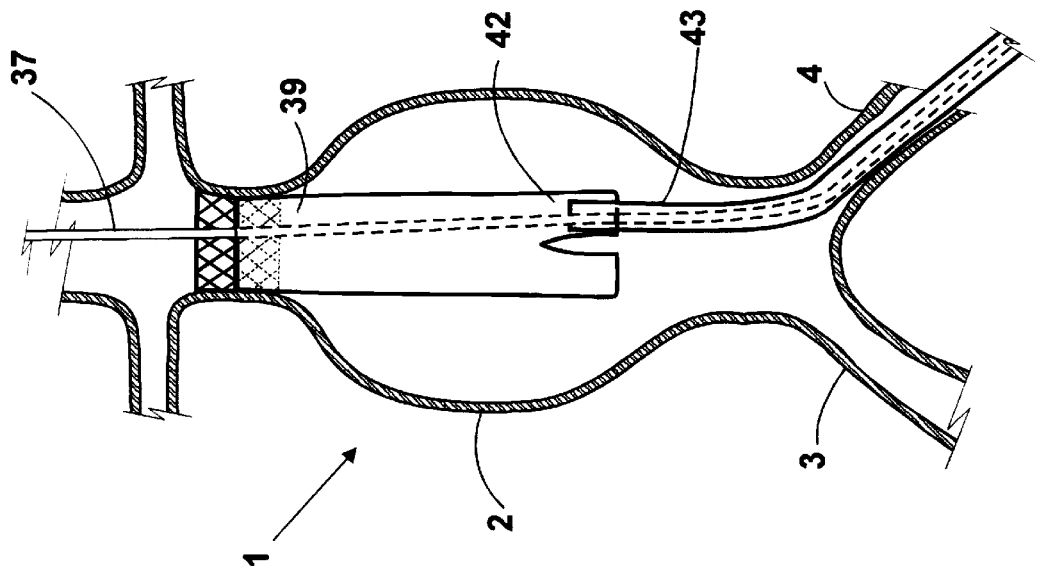
FIG. 8 shows a side elevation, partial cross-sectional view of the aorta and graft trunk portion of FIG. 7 with a leg-positioning device passed through the graft trunk portion and ready for positioning a graft leg portion according to the invention.

Also according to the method of the invention, the two remaining parts of the inventive graft, leg portions 34 and 35, are inserted into the aorta and connected to main portion 33. Once guide wire 37 has been upwardly removed from connecting end 41 as shown in FIG. 7 and trunk portion adopted its final position, the guide wire is inserted again by upper neck 39 and may pass through the best orientated of ends 41 or 42, in this case end 42 as shown in FIG. 8, to follow then through a femoral artery of the patient. Then, a leg-positioning device 43, containing one loaded folded leg portion, for example right portion 16, and respective stents 44, 45, at respective upper and lower ends 46, 47, of the leg portion, is conveyed over guide wire 37, entering the patient's body by a femoral artery and entering the aorta by iliac artery 4 into end 42 until device 43 is at the position shown in FIG. 8. Once in this position, guide wire 37 is upwardly removed from positioning device 43 and replaced by a new guide wire 48, see FIG. 9, wire 48 being inserted into device 43 by a rear end of device 43, to give support to the positioning device 43 inside the trunk portion. Guide wire 37 is upwardly removed just to be released from device 43 and is inserted through connecting end 41 to enter iliac artery 3 and another leg-positioning device 49 is inserted over guide wire 37 in like manner that device 43, but through an incision in the other groin of the patient. The positioning device 49 carries leg portion 35 and stents 50 and 51 respectively fixed at upper end 52 and lower end 53 of the left leg portion. Once in this position, devices 48, 49 are moved backwards as it is shown by the arrows in FIG. 9, to then deploy leg portions 34, 35. Therefore, as illustrated in FIG. 9, trunk portion 33 is installed in the aorta free of any twisting effect or rotation, with both leg portions 34, 35, in position to be simultaneously deployed, each one over guide wires 37, 48, respectively.

The balloons are inflated to deploy stents 44, 45, 50, 51 to place the graft portions into the configuration shown in FIG. 10, thus the leg portions being firmly attached to trunk portion 33 and to iliac arteries 3, 4. Additional stents, not shown, may be used between stents 44, 45 and 50, 51, or only one long entire stent, as it is well known in the art, to avoid any possibility of graft leg kinking. Like stent 38, stents 44, 45, 50, 51 may be of a resilient type or may be of the rigid type as well as they are made of any suitable biomedical grade metal. If the resilient type is used, no balloons may be necessary.

Figure 11:
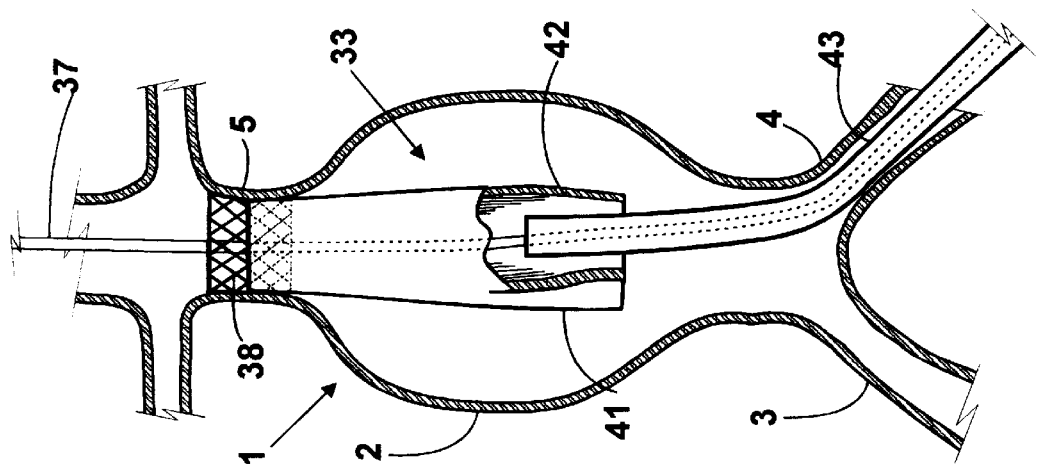
FIG. 11 shows a side elevation, partial cross-sectional view similar to FIG. 8 but with the trunk portion positioned close to a less favorable condition having the bifurcation rotated about 90° relative to the alignment of the iliac arteries, with a leg-positioning device passed through the graft trunk portion and ready for positioning a graft leg portion according to the invention.

In connection to FIGS. 11–13 a lesser favorable situation will be described in connection to the final position of the trunk portion after installation. FIG. 11 shows trunk portion 33 attached to aortic neck 5 and rotated closely 90° relative to the position shown in FIGS. 7–10, that is with connecting left and right ends 41, 42, respectively, aligned in a cross configuration relative to iliac arteries 3 and 4. This would represent a major obstacle for the installation of a conventional one-piece bifurcated graft because at this stage at least one of the limbs would be also inserted into one of the iliac arteries, therefore, at the steps of deploying the trunk and the limbs a twisting effect appears along the graft, the twisted graft being unable of releasing the twist because two opposite ends of the one-piece graft are already retained in neck 5 and one of the arteries. According to the invention, when the guide wire used for inserting trunk portion into the aorta is removed, ends 41 and 42 are free to rotate and adopt the final position without any twist affecting the material.

Like in the situation disclosed in connection to FIGS. 3–10, guide wire 37 is inserted into the aorta and one trunk-positioning device 36, shown in the step illustrated in FIG. 6, is introduced over the guide wire, through an iliac artery, the positioning device containing the trunk portion to be deployed inside the aorta. Trunk portion 33 is then deployed against aortic neck 5, undergoing a twisting effect like the one shown in FIG. 6, with trunk-positioning device 36 being removed backwards and guide wire 37 upwardly removed from the trunk portion. Once the trunk portion is released from the guide wire, the trunk portion becomes relaxed and is free to rotate, whereby the twisting effect disappears from the trunk and the trunk remains freely moving and oriented as shown in FIG. 11. Guide wire 37 is then reinserted into trunk portion 33 and passed to any of the connecting ends 41, 42, to be directed to any of the corresponding iliac arteries 3, 4. Although connecting ends 41 and 42 are not directly aligned with the corresponding iliac arteries 3 and 4, guide wire 37 will pass either through connecting end 41 or through connecting end 42 to then enter either into artery 3 or artery 4. While guide wire is illustrated as passing through end 42 and artery 4, the guide wire may have passed through end 42 and artery 3, or through end 41 and artery 4, without any twist, fold or restriction appearing on the graft. Leg-positioning device 43 is then inserted over guide wire 37, the leg-positioning device containing one loaded folded leg portion, for example right leg portion 34 and stents 44, 45, at upper and lower ends 46, 47 of the leg portion. Device 43 is inserted into the patient's body by a femoral artery and entering the aorta by iliac artery 4, until device 43 is at the position shown in FIG. 11.

Figure 12:
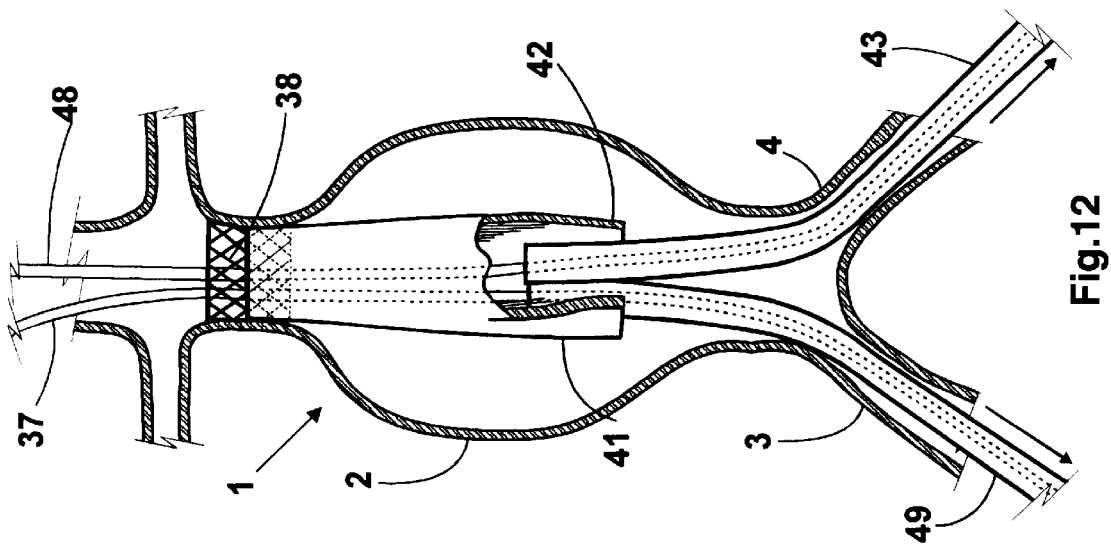
FIG. 12 shows a side elevation, partial cross-sectional view of the aorta and graft trunk portion similar to FIG. 9, with both introducing or positioning devices containing the leg portions ready to be deployed in place within the aorta and the iliac arteries.

Once in this position, guide wire 37 is upwardly removed from positioning device 43 and simultaneously may be replaced by a new guide wire 48, see FIG. 12, and the procedure is similar to the one disclosed in connection to FIGS. 6–10, that is wire 48 is inserted into device 43, at a rear end thereof, to give support to the leg-positioning device inside the trunk portion. Guide wire 37, once released from device 43, is inserted through connecting end 41 to enter iliac artery 3 and another leg-positioning device 49 is inserted over guide wire 37 in like manner that device 43, but through an incision in the other groin of the patient, see FIG. 12. The leg-positioning devices carry leg portions 34, 35 with stents 44, 45, 50, 51 respectively fixed at the ends of the leg portions. Once in this position, devices 43, 49 are moved backwards as it is shown by the arrows in FIG. 12, to allow leg portions 34, 35 to be deployed. Therefore, as illustrated in FIG. 12, trunk portion 33 is installed in the aorta free of any twisting effect or rotation, with both leg portions 34, 35, in position to be simultaneously deployed, each one over guide wires 48, 37, respectively.

Figure 13:
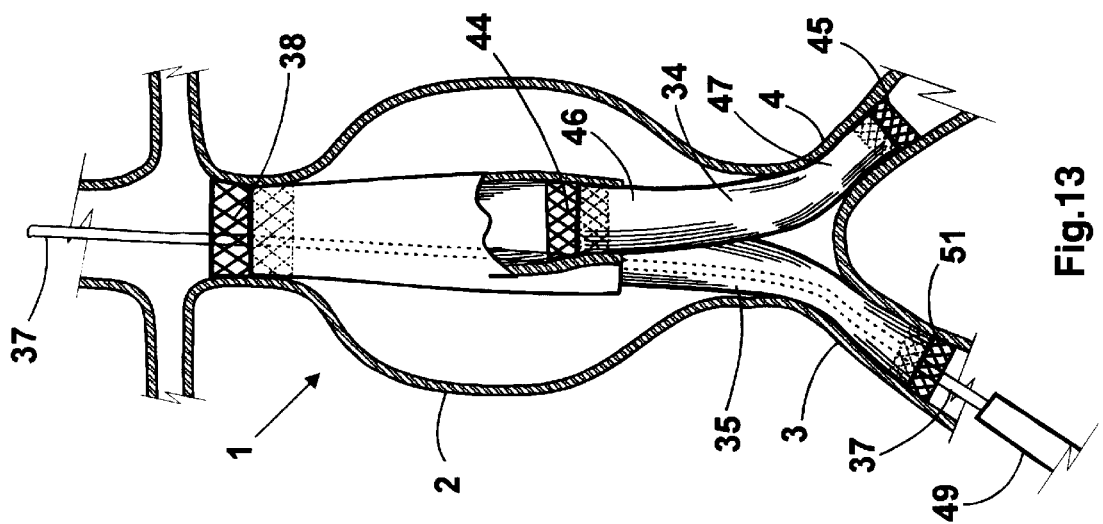
FIG. 13 shows a side elevation, partial cross-sectional view of the aorta, the graft trunk portion and the leg portions installed inside the iliac arteries.

The balloons are inflated to deploy stents 44, 45, 50, 51 to place the graft portions into the configuration shown in FIG. 13, thus the leg portions being firmly attached to trunk portion 33 and to iliac arteries 3, 4. Additional stents, not shown, may be used between stents 44, 45 and 50, 51 (not shown), as it is well known in the art, to avoid any possibility of kinking. Like stent 38, stents 44, 45, 50, 51 may be of a resilient type or may be of the rigid type as well as they are made of any suitable biomedical grade metal. If the resilient type is used, no balloons may be necessary.

Graft iliac leg portions 34 and 35 are generally cylindrical elongated sleeves with an upper and lower ends duly designed to ensure a firm a sealed connection with connecting ends 41 and 42 of the trunk portion. Connecting ends 41 and 42 may have tapered configurations to form an interference with the upper end of the associated leg portion, or any other kind of diameter interference may be performed by a clamp or suture made at ends 41 and 42, before installation, so as to restrict the diameter of ends 41 and 42. One of the ends or pending legs 41, 42 may also be closed by suture, a clamp, etc. to convert the bi-iliac graft into a monoiliac graft. This reform may be also carried out according to the embodiment of the invention shown in FIG. 18, with a thread passing through the graft material at a bifurcation point of pending legs 41, 42. Graft portions 33, 34, 35 may be manufactured from any suitable textile or fabric material, at least partially elastic or inelastic, either a woven or a knitted material.

In general terms, the invention provides a method for intraluminally positioning and implanting the aortic bifurcated graft 33, 34, 35 by acceding to aorta 1 by a guide wire inserted through an aortic neck or an end neck of an aneurysm, the graft being inserted through a blood vessel, preferably femoral or iliac arteries 3, 4, wherein the bifurcated graft is implanted by first placing trunk portion 33 against upper proximal aortic neck 5 and then installing each secondary leg portion 34 and 35 in each corresponding iliac artery 3 and 4 and connecting trunk portion 33 to leg portions 34, 35, whereby each leg portion is attached to one iliac artery and to the main trunk portion once any rotation of trunk portion 33, produced by the deployment and installation of the main trunk portion had already occurred, whereby no rotation or twisting of the graft main trunk portion is transferred to the graft leg portions.

More particularly, the method of the invention comprises the steps of inserting guide wire 37 in a blood vessel at a site remote to the site of aorta 1 affected by the aneurysm and moving the guide wire to make it enter the aneurysm by the aortic upper neck, inserting graft trunk portion 33 over the guide wire by means of trunk-positioning device 36 including at least one expandable balloon, with the graft trunk portion being maintained in a compressed condition inside the trunk-positioning device with the upper end of the graft trunk portion over the balloon, positioning the graft trunk portion inside the aorta at the site of the aneurysm and deploying the graft trunk portion by inflating the balloon, whereby upper end 39 of the graft trunk portion is securely attached to aortic neck 5 while lower connecting ends 41 and 42 remain free to move and float; permitting lower connecting ends 41, 42 to rotate relative to upper end 39, whereby the connecting ends remain in a relaxed condition after upper end 39 has been attached to the aorta; downwardly removing the positioning device; upwardly move guide wire 37 within the installed graft trunk portion and above the connecting ends in an extent enough to be then capable of being downwardly moved and introduced through one of the connecting ends; moving guide wire 37 downwardly, making guide wire pass through one of the connecting ends 41, 42, and enter one of the iliac arteries 3, 4, introducing the above mentioned positioning device 36 or leg-positioning device 43 over the above mentioned guide wire 37, passing through the one 42 connecting end and the one 4 iliac artery, positioning device 43 as shown in FIG. 11, device 43 carrying the graft leg portion in a compressed condition with the upper end of the graft leg portion over one of the balloons of the positioning device. The leg portion may be deployed at this stage or, preferably, may remain in place to be deployed simultaneously with the other leg portion by inflating a corresponding balloon when the upper end of the graft leg portion is inside the one lower connecting end of the graft trunk portion and the lower end of the leg portion is inside the one iliac artery, whereby the upper end of the graft leg portion may be radially expanded and securely attached against the one lower connecting end of the graft main portion, to connect the graft trunk and leg portions in fluid flow communication; upwardly removing wire 37 out of device 43 and inserting a new guide wire 48 through a rear end of device 43 to give support to device 43 within the aorta. Wire 37 is upwardly moved just to be released from device 43 and is inserted the other 41 of the connecting ends and enter the other 3 of the iliac arteries; introducing another leg-positioning device 49 over guide wire 37 passing through the other connecting end 41 and the other iliac artery 3, the another leg-positioning device 49 carrying another graft leg portion 35 in a compressed condition with the upper end of the graft leg portion over one of the balloons of the positioning device; deploying the graft leg portion by inflating a corresponding balloon when the upper end of the graft leg portion is inside the other 41 lower connecting end of the graft trunk portion and the lower end of the leg portion is inside the other 3 iliac artery, whereby the upper end of the graft leg portion is radially expanded and securely attached against the other lower connecting end 41 of the graft trunk portion, with the graft trunk portion and the other leg portion being connected in fluid flow communication; and removing the positioning devices and guide wires.

With the inventive graft and method of the invention the drawbacks of conventional bifurcated grafts and implanting methods are avoided, or at least minimized. Both, the rotation generated during the installation of a conventional graft, and the lack of flexibility of compliance to accommodate to the tortuous vessels shapes, are overcome with the teachings of the invention. With the present invention, the rotation of graft portion 33 is accommodated as long as ends 41 and 42 are free to rotate once end 39 has been retained inside neck 5, therefore the twisting effect does not occur in the tubular body of graft 33 because ends 41 and 42 rotate in the same extent that end 39 has rotated. Then, leg portions 34, 35, are installed as above explained.

Another important aspect of the invention is related to the use of anchoring means of the resilient type, that is self-expanding stents. The twisting effect to which wide reference has been made in connection to the use of rigid stents may also appear when using resilient stents because the graft is longitudinally placed within the tubular positioner, applicator or introducer and, when the graft is left to move out the applicator the stents are released in a no simultaneous pattern. Under these circumstances, if graft 25 (FIG. 5) is being installed stent 29 is first expanded with the usual rotation thereof while one of stents 30 or 31 still remains inside the positioning device, thus the rotation of one or both stents 30, 31 generates a twisting effect along sleeve 25 and this twisting effect may be increased by any rotation of the positioning device when moving during the removal thereof to leave one stent 30 or 31 expanded in a position rotated relative to stent 29. Therefore, the fact of leaving connecting ends to freely rotate after stent 38 has been attached to neck 5 makes the graft to accompany the rotation of the stent thus preventing the graft from being twisted or folded.

When reference has been made in the present application to right and left iliac arteries or leg portions, the left and right hands are referred to the left and right sides of the figures.

According to another aspect of the invention related to the connection between the parts or portions forming part of the above disclosed monoiliac and bi-iliac grafts, another embodiment of the application, illustrated in FIGS. 16–18, prevents the parts of the graft from accidentally detaching during the use of the graft, foreseen for the entire patient's life.

Once the main portion of the graft, either the main portion of a monoiliac graft, such as the one illustrated in FIGS. 2–4, or the trunk portion of a bi-iliac graft, such as the one shown in FIGS. 6–13, the lower end of the main/trunk graft portion must be connected to a lower leg portion/portions also forming part of the entire graft. This connection is established by means of a stent firmly retained within the leg portion and the leg portion is inserted into the lower end of the upper main or trunk graft portion. Once in this position, the stent is expanded, either by its own elastic memory or by a balloon to make the leg portion to be firmly retained against the main or trunk portion. This is an easy task in the case of a graft made of an inelastic, i.e. not compliant, woven fabric but a firm connection is not achieved by this procedure when the fabric is a knitted elastic, compliant fabric, as will be explained in connection to FIGS. 14–18.

To explain the conventional connection between two graft parts a monoiliac graft of the prior art has been illustrated in FIGS. 14 and 15, where new reference numbers have been used for the graft but the same numbers are kept to identify the aorta and its portions. The monoiliac graft comprises a main upper portion 53 having a lower portion tapered towards a lower edge 55 so that a diameter D1 of this edge is the smallest one as compared to any other diameter D2 in the upper portions of the main portion. An upper or leading end 56 of a lower leg graft portion 57 is inserted into portion 54 in a manner that anchoring means, such as a stent 58, firmly connected to end 56 remains within of portion 54 whereby the stent, once expanded by any know procedure as explained above, remains as illustrated in FIGS. 14, 15, retained against an inner surface of portion 54 thus making the connection between portion 53 and leg portion 57 to be firmly retained against any forces from the blood flow. As explained above, this connection may be firmly maintained thank to the fact that at least main portion 53 is manufactured from an inelastic, non compliant fabric, thus making the stent to be retained against the tubular fabric. In addition, the tapered configuration of portion 54 prevents the expanded stent from being downwardly move out of lower edge 55. However, inelastic woven fabrics do not fully accommodate to sizes, irregularities and diameters of the blood vessels, particularly the inner diameter of the upper aortic neck and the iliac arteries. This drawback, however, can not be overcome by merely selecting a larger diameter when the surgeon has found that the maximum diameter of the graft is smaller than the diameter of the vessel. In this situation, if a graft having a larger diameter is used for a vessel having a diameter smaller than the one of the graft, then the exceeding graft material will remain folded against the vessel wall with the known consequences resulting in leaking between the graft and the vessel wall, particularly the aortic neck wall.

In view of the above explained drawbacks the compliant elastic materials are expected to be more frequently used, replacing the inelastic materials. The compliant materials, however, do not behave like the inelastic materials when performing connections of the type disclosed above and shown in FIGS. 14 and 15. As disclosed in connection to such Figures, the material of portion 54 must exert a counter force against the expansion of stent 58 without yielding upon the expansion force of the stent. Compliant materials can not behave in this way and the connection can not be firmly maintained, even if a tapered configuration like the one shown in FIGS. 14, 15 is adopted for the graft parts.

According to the embodiments of the invention shown in FIGS. 16–18, it is possible to take advantage of the benefits of the compliant material without being affected by the drawbacks of this material. Briefly, the compliance of the material will be used for the parts of the graft where this quality is necessary while the portion or portions of the graft where the elasticity is inconvenient will be inelastic and capable of retaining a predetermined fixed diameter.

The graft of the invention comprises a monoiliac or a bi-iliac graft consisting of two, three or more parts, as it was widely explained above in connection to the other embodiments of the invention. The concepts of the invention will be now explained as applied to a monoiliac graft for simplicity purposes. The inventive graft comprises an upper main portion 59 having an upper edge 60, a lower edge 61 and preferably a tapered middle portion 62 that is tapered towards edge 61. Graft portion 62 may be manufactured from any compliant material, such as a knitted fabric material with controlled expansion, even along the entire life of the graft, as it will be very well known for any person skilled in the art. The material is preferably a knitted fabric manufactured in a circular loom, as it is also well know to any one skilled in the art. The teachings of the inventions are applied to edge 61, as well as to any other part of the graft that it is desired to have an inelastic behavior for purposes of operation as will be explained below.

In FIG. 17 a preferred knitted construction has been illustrated but it is to be remarked that any other construction may be used as long as the concepts of the invention can be applied to the same. As explained in connection to FIGS. 14, 15, a firm connection must be guaranteed between the upper main graft portion and the lower leg portion. In FIG. 16, a stent must be, therefore, firmly retained within lower portion 62 of graft portion 59 but, the elastic construction of the graft would not guarantee such desired retention. To assure the desired retention a thread, either inelastic or controllably elastic, is arranged at the edge, close to the edge or portion of the graft desired to be converted into inelastic.

To prevent a stent 64 to slip off or detach from its retention against the wall 63 of the graft a thread 65 is threaded through the edge loops 66 of the knitted textile as better shown in FIG. 17, and a knot 67 may be made by the physician, his/her assistant or the manufacturer at free ends 71 of the thread before installing the graft into the introducer. Thus the diameter of lower edge 61 is restricted to a predetermined maximum value, this predetermined diameter being related to the maximum diameter to which stent 64 may be, or are to be, expanded, whereby the stent, and hence a leg portion 68, is firmly retained against graft portion 62 and prevented to slip off by thread 65. The stent should be expanded at such an extent that, in the expanded condition, will have a maximum diameter larger than the predetermined maximum diameter of the inelastic edge.

A similar thread 69 may be arranged through loops 70 in upper edge 60, however, this thread is not knotted as long as edge 60 should preferably remain entirely elastic to accommodate to the upper aortic neck and its irregularities. Threads 65, 69 may be passed through the outermost loops 66, 70 as illustrated or may be conveniently passed through a more inner row of loops. Threads 66, 70 may be threaded after the fabric has been manufactured or may be knitted or threaded during the knitting of the fabric, that is forming part of the fabric construction, thus the thread does not threaded on purpose after the knitted fabric has been manufactured. Although the thread has elastic characteristics the elastic elongation the thread can be adopted is always shorter than the one that the knitted fabric can reach because of its yielding capacity provided by the knitting characteristics. That is the elasticity of the thread is a controlled elasticity.

The concept of using a thread either to be knotted to restrict a diameter or to remain free is also used in the embodiment shown in FIG. 18, wherein a bifurcated graft trunk portion 72, like the ones disclosed above, is shown. Graft portion 72 incorporates the teachings of the diameter restricting thread in pending leg 73 wherein a thread 74 is arranged to a lower edge 75. The construction may be the same or similar to the one shown in FIG. 17 and the thread may be knotted to restrict the diameter of edge 75 with the same above explained retention purposes. In another application, pending leg 76 may include an additional thread 77, passed through the known typical loops of the knitted fabric, with the purpose of pulling from the thread and knotted the same to close leg at a point close to a bifurcation 78 of the graft, in order to convert the bi-iliac aortic graft into a monoiliac aortic graft.

Also in accordance with the present invention, a new method for treating abdominal aortic aneurysms are provided, the method comprising the steps of providing graft 59 to be intraluminally inserted in the aorta, the aorta having an upper proximal aortic neck and a distal aortic lower portion forming an iliac bifurcation dividing into two iliac arteries. According to the inventive method, the main portion of the graft is placed inside the aorta whereby the portion is firmly retained against the upper aortic neck with lower edge 61 of the graft main portion freely moving inside the aneurysm, then, the upper end of leg portion 68 is inserted inside the lower portion of the main graft portion, and the anchoring means comprising the stent 64 is expanded once at least a part of the stent is inside lower portion 62 and upwardly lower inelastic edge 61. Stent 64 is expanded to an extent to define, in the expanded condition, and in at least a section thereof upwardly edge 61, a maximum diameter larger than a predetermined maximum diameter of edge 61, whereby the upper end of the leg portion may be retained within the lower portion of the main portion by the anchoring means, with the inelastic edge encircling the upper end of the graft leg portion and the stent remaining within the graft main portion upwardly of edge 61.

However, as stated above, only part of the stent need be placed inside lower portion 63, upwardly edge 61, that is stent 64 does not need to be entirely located upwards edge 61 (as it is shown in FIG. 16) to provide a firm retention and reliable sealing. This configuration may be preferably used when leg portion 68 includes a plurality of stents, or a long unique stent, along its length. That is, a leg portion stented at the ends thereof or entirely stented with one long or several short stents.

According to a preferred embodiment of the invention the method preferably comprises the step of making a knot in free ends 71 of the thread in order to define a predetermined maximum diameter of the inelastic edge before placing the main graft portion inside the aorta. Here again, the stent defines, in the expanded condition, a maximum diameter larger than the predetermined maximum diameter of the inelastic edge.

While preferred embodiments of the present invention have been illustrated and described, it will be obvious to those skilled in the art that various changes and modifications may be made therein without departing from the scope of the invention as defined in the appended claims. For example, while a flat material has been shown for all of the embodiments of the invention, a curled or draped material may be used to facilitate the accommodation thereof to the vessel shapes.

I claim:

1. An aortic graft for treatment of abdominal aortic aneurysms, the graft comprising a tubular hollow material for intraluminal insertion in the aorta, the aorta having an upper proximal aortic neck and a distal aortic lower portion forming an iliac bifurcation dividing into two iliac arteries, the graft comprising:
   a compliant graft main portion having a generally cylindrical shape with an upper end for secure attachment to the aortic proximal neck, and a lower free end constructed so as to wholly reside at a position inside the aneurysm and above the iliac bifurcation, and
   at least one compliant graft iliac leg portion having a generally elongated cylindrical shape with a lower end for secure attachment to one of the iliac arteries, and an upper end for secure attachment in fluid communication to the lower end of the graft main portion.

2. The graft of claim 1, wherein the graft leg portion has a diameter slightly larger than the diameter of the graft main portion, the diameter of the graft main portion decreasing towards the lower end thereof to securely receive the upper end of the graft leg portion inside the lower end of the graft main portion.

3. The graft of claim 2, wherein the upper end of the graft leg portion is retained within the lower end of the graft main portion by anchoring means.

4. The graft of claim 3, wherein the anchoring means is fixed into the upper end of the graft leg portion and is securely attached to the graft main portion by a radially expandable balloon removably placed by a catheter, whereby the anchoring means is implantable by expansion against the graft main portion, at an overlap between the lower end of the graft main portion and the upper end of the graft leg portion, both ends being securely retained to each other.

5. The graft of claim 4, wherein anchoring means is fixedly located into the lower end of the graft leg portion and is securely attached to the iliac artery by a radially expandable balloon removably positioned by the catheter, whereby the anchoring means is implantable by expansion against the artery.

6. The graft of claim 2, wherein the upper end of the graft leg portion is retained within the lower end of the graft main portion by a diameter interference.

7. A method of treating abdominal aortic aneurysms with the graft of claim 1, comprising the steps of:
   inserting a guide wire in a blood vessel at a site remote to the site of an aorta affected by the aneurysm and moving the guide wire to make it enter the aneurysm by the aortic upper neck,
   inserting the graft main portion over the guide wire by means of a positioning device entering the aneurysm by an iliac artery, the positioning device including at least one expandable balloon, with the graft main portion being maintained in a compressed condition inside the positioning device with least the upper end of the graft main portion located over the balloon,
   positioning the graft inside the aorta at the site of the aneurysm and deploying the graft main portion by inflating the balloon, whereby the upper end of the graft main portion is securely attached to the proximal upper aortic neck,
   downwardly removing the positioning device,
   permitting the lower end of the graft main portion to freely rotate relative to the upper end of the graft main portion to unfold/untwist and accommodate any rotation of the upper end generated during deploying and installation of the main graft, whereby the lower end remains in a floating or moving free relaxed condition after the upper end of the main portion has been attached to the aorta, and
   introducing the same positioning device or a new positioning device over the guide wire, the positioning device carrying at least one balloon and the graft leg portion in a compressed condition with at least the upper end of the graft leg portion over the balloon of the positioning device, and deploying the graft leg portion by inflating at least one balloon when the upper end of the graft leg portion is inside the lower end of the graft main portion and the lower end of the leg portion is inside a corresponding iliac artery, whereby the ends of the graft leg portion are radially expanded and securely attached against the lower end of the graft main portion and the corresponding iliac artery, with the graft main and leg portions being connected in fluid flow communication.

8. The method of claim 7, wherein the upper end of the graft leg portion is provided with anchoring means capable of being expanded by the balloon and remains in the expanded condition to retain the upper end of the graft leg portion against the lower end of the graft main portion.

9. The method of claim 8, wherein the expansion of the anchoring means at the upper end of the graft leg portion is carried out simultaneously with an expansion of anchoring means located at least at the lower end of the graft leg portion, whereby the lower end of the graft leg portion is implanted within and against one of the iliac arteries simultaneously with the attaching of the upper end of the graft leg portion to the lower end of the graft main portion.

10. The graft of claim 1, wherein anchoring means are provided at the upper end of the graft main portion and at the upper and lower ends of the graft leg portion.

11. The graft of claim 10, wherein the anchoring means are of a resilient self-expanding type.

12. A method of treating abdominal aortic aneurysms with the graft of claim 11, comprising the steps of:

inserting a guide wire in a blood vessel at a site remote to the site of an aorta affected by the aneurysm and moving the guide wire to make it enter the aneurysm by the upper aortic neck, inserting the graft main portion over the guide wire by means of a positioning device entering the aneurysm by an iliac artery, the positioning device including the graft main portion and a self-expanding anchoring means maintained in a compressed condition inside the positioning device, positioning the graft main portion inside the aorta at the site of the aneurysm and deploying the graft main portion by permitting the expandable anchoring means to freely expand, whereby the upper end of the graft main portion is securely attached to the proximal aortic neck while the lower end of the graft main portion remains free to rotate, downwardly removing the positioning device, permitting the lower end of the graft main portion to rotate relative to the upper end of the graft main portion, to accommodate any rotation of the main portion generated during deployment and installation thereof, whereby the lower end of the main portion remains in a relaxed condition after the upper end of the main portion has been attached to the aorta, and introducing the same positioning device or a new positioning device over the guide wire, the positioning device being inserted by the iliac artery and carrying the graft leg portion with associated self-expanding anchoring means in a compressed condition, and deploying the graft leg portion by permitting the anchoring means to freely expand when the upper end of the graft leg portion is inside the lower end of the graft main portion and the lower end of the leg portion is inside the iliac artery, whereby the ends of the graft leg portion are radially expanded and securely attached against the lower end of the graft main portion and the iliac artery, with the graft main and leg portions being connected in fluid flow communication.

13. The graft of claim 1, comprising an inelastic woven material, the graft main portion having a generally cylindrical shape with a lower portion tapered towards the lower end of the main portion, the upper end of the leg portion being retained within the tapered lower portion by anchoring means.

14. The graft of claim 1, comprising an inelastic woven material, the graft main portion having a generally cylindrical shape with a lower end of the main portion being a cone-shaped portion the diameter of which decreases towards a lower edge of the main portion, the upper end of the leg portion being retained within the tapered lower end by anchoring means.

15. A method for intraluminally positioning and implanting an aortic graft according to claim 1, by acceding to an aorta through any blood vessel connected to the aorta, preferably an iliac artery, wherein the graft is implanted by first placing a main portion of the graft against an upper proximal aortic neck and then installing a secondary leg portion in the corresponding iliac artery and connecting the main and leg graft portions to each other inside the aorta, whereby the leg portion is attached to the iliac artery and to the main portion once any rotation of the main portion, produced by the deployment and installation of the main portion, has already occurred, whereby no rotation or twisting of the graft main portion is transferred to the graft leg portion.

16. An aortic bifurcated graft for treatment of abdominal aortic aneurysms, the graft comprising a tubular hollow material for intraluminal insertion in the aorta, the aorta having an upper proximal aortic neck and a lower distal portion defining an aortic bifurcation dividing into two iliac arteries, the graft comprising:

a compliant graft trunk portion made of a flexible fabric material, the portion having a generally cylindrical shape with an upper end for secure attachment to the aortic proximal neck, and a lower bifurcated short portion forming two lower side-by-side connecting ends, the connecting ends constructed so as to wholly reside inside the aorta and upwardly and spaced apart from the aortic bifurcation, and a pair of compliant graft iliac leg portions made of a flexible fabric material, each portion having a generally elongated cylindrical shape with a lower end for secure attachment to one of the iliac arteries, and an upper end for secure connection in fluid communication to a respective one of the lower connecting ends of the lower bifurcated portion of the trunk portion.

17. A method of treating abdominal aortic aneurysms with the graft of claim 16, comprising the steps of:

inserting a guide wire in a blood vessel at a site remote to the site of an aorta affected by the aneurysm and moving the guide wire to enter the aneurysm by the upper aortic neck, inserting the graft trunk portion over the guide wire by means of a trunk-positioning device entering the aneurysm by an iliac artery and including at least one expandable balloon, with the graft trunk portion being maintained in a compressed condition inside the positioning device with at least the upper end of the graft trunk portion located over the balloon, positioning the graft trunk portion inside the aorta at the site of the aneurysm and deploying the graft trunk portion by inflating the balloon, whereby the upper end of the graft trunk portion is securely attached to the proximal aortic neck while the lower connecting ends of the graft trunk portion remain inside the aorta and above the aortic bifurcation, downwardly removing the trunk-positioning device and upwardly moving the guide wire inside the installed graft trunk portion and above the connecting ends, permitting the lower connecting ends of the graft trunk portion to follow any rotation of the upper end of the graft trunk portion generated by the balloon during inflation thereof, whereby the lower connecting ends remain in a free moving or floating relaxed condition after the upper end of the trunk portion has been attached to the aorta, without the trunk portion being affected by any twisting effect, introducing the guide wire through one of the connecting ends and making the guide wire enter one of the iliac arteries, introducing a leg-positioning device over the guide wire passing through the one connecting end of the trunk portion and the one iliac artery, the leg-positioning device carrying at least one balloon and one graft leg portion in a compressed condition with the upper end of the graft leg portion over the balloon of the leg-positioning device, and deploying the graft leg portion by inflating the balloon when the upper end of the graft leg portion is inside the one lower connecting end of the graft trunk portion and the lower end of the leg portion is inside the one iliac artery, whereby at least the upper end of the graft leg portion is radially expanded and securely attached against the one lower connecting end of the graft main portion and the iliac artery, with the graft trunk and leg portions being connected in fluid flow communication, downwardly removing the leg-positioning device and upwardly removing the guide wire, introducing a guide wire through the upper end of the installed trunk portion and make the guide wire pass through the other of the connecting ends and enter the other of the iliac arteries, introducing another leg-positioning device over the guide wire passing through the other connecting end and the other iliac artery, the another leg-positioning device carrying another graft leg portion in a compressed condition with at least the upper end of the graft leg portion over the balloon of the another leg-positioning device, and deploying the graft leg portion by inflating the balloon when the upper end of the graft leg portion is inside the other lower connecting end of the graft trunk portion and the lower end of the leg portion is inside the other iliac artery, whereby at least the upper end of the graft leg portion are radially expanded and securely attached against the other lower connecting end of the graft trunk portion and the other iliac artery, with the graft trunk portion and the other leg portion being connected in fluid flow communication, and downwardly removing the positioning device and upwardly removing the guide wire.

18. The method of claim 17, wherein the upper end of each graft leg portion is provided with anchoring means each capable of being expanded by a balloon and remains in the expanded condition to retain the respective upper end of the graft leg portion against the respective lower connecting end of the graft trunk portion.

19. The method of claim 18, wherein the expansion of the anchoring means at the upper end of each graft leg portion is carried out simultaneously with an expansion, made by the balloon, of anchoring means located at least at the lower end of each graft leg portion, whereby the lower end of each graft leg portion is implanted within and against a respective one of the iliac arteries simultaneously with the attaching of the upper end of each graft leg portion to the respective one of the lower connecting ends of the graft trunk portion.

20. The method of claim 17, wherein the guide wire enters the graft trunk portion through the upper end of the trunk portion, while the positioning devices enter the graft over the guide wire, through the connecting ends, via corresponding femoral arteries.

21. A method of treating abdominal aortic aneurysms with the graft of claim 16, comprising the steps of:

inserting a guide wire in a blood vessel at a site remote to the site of an aorta affected by the aneurysm and moving the guide wire to enter the aneurysm by the upper aortic neck, inserting the graft trunk portion over the guide wire by means of a trunk-positioning device entering the aneurysm by an iliac artery and including at least one expandable balloon, with the graft trunk portion being maintained in a compressed condition inside the trunk-positioning device with at least the upper end of the graft trunk portion located over the balloon, positioning the graft trunk portion inside the aorta at the site of the aneurysm and deploying the graft trunk portion by inflating the balloon, whereby the upper end of the graft trunk portion is securely attached to the proximal aortic neck while the lower connecting ends of the graft trunk portion remain inside the aorta and above the aortic bifurcation, downwardly removing the trunk-positioning device and upwardly moving the guide wire within the installed graft trunk portion and above the connecting ends, permitting the lower connecting ends of the graft trunk portion to rotate, following any rotation of the upper end of the graft trunk portion, generated during the inflation of the balloon, whereby the lower connecting ends remain in a free moving/floating relaxed condition after the upper end of the trunk portion has been attached to the aorta, without the trunk portion being affected by any twisting effect, introducing the guide wire through one of the connecting ends and making the guide wire enter one of the iliac arteries, introducing a leg-positioning device over the guide wire passing through the one connecting end and the one iliac artery, the leg-positioning device carrying at least one balloon and a graft leg portion in a compressed condition with at least the upper end of the graft leg portion over the balloon of the leg-positioning device, moving the guide wire out of the positioning device and above the connecting ends and simultaneously placing a new guide wire inserted into the leg-positioning device through a rear end of the leg-positioning device, while the leg-positioning device remains inside the trunk portion, downwardly moving the guide wire through the upper end of the installed trunk portion and making the guide wire pass through the other of the connecting ends and enter the other of the iliac arteries, introducing another leg-positioning device over the guide wire passing through the other connecting end and the other iliac artery, the another leg-positioning device carrying at least one balloon and another graft leg portion in a compressed condition with at least the upper end of the graft leg portion over the balloon of the positioning device, deploying the graft leg portions by inflating the balloons when the upper ends of the graft leg portions are inside the corresponding lower connecting ends of the graft trunk portion and the lower ends of the leg portions are inside the iliac arteries, whereby at least the upper end of the graft leg portions are radially expanded and securely attached against the lower connecting ends of the graft trunk portion, with the graft trunk portion and the leg portions being connected in fluid flow communication, and downwardly removing the leg-positioning devices and the new guide wire, while the guide wire is upwardly removed.

22. The method of claim 21, wherein the upper end of each graft leg portion is provided with anchoring means each capable of being expanded by a balloon and remain in the expanded condition to retain the respective upper end of the graft leg portion against the respective lower connecting end of the graft trunk portion.

23. The method of claim 22, wherein the expansion of the anchoring means at the upper end of each graft leg portion is carried out simultaneously with an expansion, made by one balloon, of anchoring means located at least at the lower end of each graft leg portion, whereby the lower end of each graft leg portion is implanted within and against a respective one of the iliac arteries simultaneously with the attaching of the upper end of each graft leg portion to the respective one of the lower connecting ends of the graft trunk portion.

24. The method of claim 21, wherein the guide wire enters the graft trunk portion through the upper end of the trunk portion and the positioning devices are introduced by the connecting ends, via corresponding femoral arteries.

25. The graft of claim 16, wherein the upper end of each graft leg portion is retained within an associated one of the lower connecting ends of the graft trunk portion by anchoring means.

26. The graft of claim 25, wherein the anchoring means is fixedly located into the upper end of each graft leg portion and is securely attached to the graft trunk portion by a radially expandable balloon removably positioned by a catheter, whereby the anchoring means is implantable by expansion against one associated connecting end of the graft trunk portion, at an overlap between the lower connecting end of the trunk portion and the upper end of the graft leg portion, both ends being securely retained to each other in fluid communication.

27. The graft of claim 26, wherein anchoring means is also fixedly located into at least the lower end of each graft leg portion and is securely attached to the respective iliac artery by a radially expandable balloon removably positioned by a catheter, whereby the anchoring means is implantable by expansion against the artery.

28. The graft of claim 16, wherein anchoring means are provided at the upper end of the trunk portion and at the upper and lower ends of the leg portions.

29. The graft of claim 28, wherein the anchoring means are of a resilient self-expandable type.

30. A method of treating abdominal aortic aneurysms with the graft of claim 29, comprising the steps of:

inserting a guide wire in a blood vessel at a site remote to the site of an aorta affected by the aneurysm and moving the guide wire to enter the aneurysm by the upper aortic neck, inserting the graft trunk portion over the guide wire by means of a trunk-positioning device with the graft trunk portion and associated self-expanding anchoring means being maintained in a compressed condition inside the trunk-positioning device, positioning the graft trunk portion inside the aorta at the site of the aneurysm and deploying the graft trunk portion by permitting the anchoring means to radially expand, whereby the upper end of the graft trunk portion is securely attached to the proximal aortic neck while the lower connecting ends of the graft trunk portion remain inside the aorta and at a position above the aortic bifurcation, downwardly removing the trunk-positioning device and upwardly moving the guide wire within the installed graft trunk portion and above the connecting ends, permitting the lower connecting ends of the graft trunk portion to follow any rotation of the upper end of the graft trunk portion, generated by the expansion of the anchoring means, whereby the lower connecting ends remain in a relaxed condition after the upper end of the trunk portion has been attached to the aorta, introducing the guide wire through one of the connecting ends and making the guide wire enter one of the iliac arteries, introducing a leg-positioning device over the guide wire passing through the one connecting end and the one iliac artery, the leg-positioning device carrying one graft leg portion with associated self-expanding anchoring means in a compressed condition, moving the guide wire out of the positioning device and above the connecting ends and simultaneously placing a new guide wire inserted into the leg-positioning device through a rear end of the leg-positioning device, while the leg-positioning device remains inside the trunk portion, downwardly moving the guide wire through the upper end of the installed trunk portion and make the guide wire pass through the other of the connecting ends and enter the other of the iliac arteries, introducing another leg-positioning device over the guide wire passing through the other connecting end and the other iliac artery, the another leg-positioning device carrying another graft leg portion with associated self-expanding anchoring means in a compressed condition, deploying the graft leg portions by permitting the expandable anchoring means to freely expand the upper ends of the graft leg portions when they are inside the lower connecting ends of the graft trunk portion and the lower ends of the leg portions are inside the iliac arteries, whereby at least the upper end of the graft leg portions are radially expanded and securely attached against the lower connecting ends of the graft main portion, with the graft trunk portion and the leg portions being connected in fluid flow communication, and downwardly removing the leg-positioning devices and the new guide wire, while the guide wire is upwardly removed.

31. The graft of claim 16, wherein each graft leg portion has a diameter slightly larger than the diameter of the corresponding lower connecting end of the trunk portion, whereby the upper end of a leg portion can be expanded and tightly sealably received inside a corresponding lower connecting end of the trunk portion.

32. The graft of claim 16, wherein the upper end of each graft leg portion is retained within an associated one of the lower connecting ends of the graft trunk portion by diameter interference.

33. The graft of claim 16, comprising an inelastic woven material, the graft trunk portion having a generally cylindrical shape with the lower connecting ends tapered by the diameter of each connecting end downwardly decreasing, the upper end of each leg portion being retained within the tapered lower connecting end of the trunk portion by anchoring means.

34. A method for intraluminally positioning and implanting an aortic bifurcated graft according to claim 16, by acceding to an aorta through a blood vessel, preferably a femoral artery, wherein the bifurcated graft is implanted by first placing a main trunk portion of the graft against an upper proximal aortic neck and then installing two leg portions in corresponding iliac arteries and connecting the main trunk portion to the leg portions, the trunk and leg portions being installed by inflating respective balloons to expand the portions, whereby each leg portion is attached to the trunk portion once any rotation and twisting of the trunk portion, produced by inflation of the balloon during the deployment and installation of the trunk portion, had already disappeared, whereby no rotation or twisting of the graft trunk portion is transferred to the graft leg portions.

35. An aortic graft for treatment of abdominal aortic aneurysms, the graft comprising a tubular hollow material to be intraluminally inserted in the aorta, the aorta having an upper proximal aortic neck and a distal aortic lower portion forming an iliac bifurcation dividing into two iliac arteries, the graft comprising:

a graft main portion having an upper end to be securely attached to the aortic proximal neck, and a lower end hanging free at a position inside the aneurysm an above the iliac bifurcation, and at least one graft iliac leg portion having a generally elongated cylindrical shape with a lower end to be securely attached to one of the iliac arteries, and an upper end to be securely connected in fluid flow communication to the lower end of the graft main portion, at least the main graft portion being made of a compliant, elastic knitted material, and the main portion terminating in an inelastic lower edge, whereby the upper end of the leg portion may be retained within the lower portion of the main portion by anchoring means, with the inelastic edge encircling the upper end of the graft leg portion and at least part of the anchoring means remaining within the graft main portion upwardly of the inelastic edge.

36. The graft of claim 35, wherein the inelastic edge is formed by an inelastic thread passing through the elastic knitted material of the graft main portion, whereby all the graft main portion is elastic except the inelastic edge of the lower end.

37. The graft of claim 36, wherein a thread is threaded around the upper end of the graft main portion, the thread being loosely threaded so that the upper end of the graft main portion keeps its elastic characteristics to be securely attached against the aortic proximal neck by an expandable anchoring means implanted therein by and expandable balloon and a catheter.

38. A method for treating abdominal aortic aneurysms by installing inside the aorta the graft according to claim 36, the method comprising the steps of:

making a knot in free ends of the thread passing through the knitted material at the lower inelastic edge to define a predetermined maximum diameter of the inelastic edge, placing the main graft portion inside the aorta whereby the portion is firmly retained against the upper aortic neck with a lower edge of the graft main portion freely moving inside the aneurysm, inserting the upper end of the leg portion inside the lower portion of the main graft portion, and expanding the anchoring means of the leg portion once the anchoring means are at least partially inside the lower portion of the graft main portion, whereby the anchoring means defining, in the expanded condition and in at least a section thereof upwardly the thread knotted in the lower inelastic edge, a maximum diameter larger than the predetermined maximum diameter of the inelastic edge, whereby the upper end of the leg portion may be retained within the lower portion of the main portion by the anchoring means, with the inelastic edge encircling the upper end of the graft leg portion and the anchoring means remaining, at least partially, within the graft main portion upwardly of the inelastic edge.

39. The graft of claim 35, wherein the graft is a bi-iliac graft with the graft main portion having a generally cylindrical bifurcated shape, assembling a pair of pants with two pending legs.

40. The graft of claim 39, wherein the inelastic edge is formed by an inelastic thread passing through the elastic knitted material of the graft main portion, at a lower edge of one of the legs of the pants, an additional inelastic thread passing through the knitted material in the other leg at a point of bifurcation of the two pending legs of the pants, whereby the other pending leg of the pants may be closed to the blood flow to convert the bifurcated graft into one monoiliac aortic graft.

41. The graft of claim 35, wherein the graft main portion has a generally cylindrical shape with the lower portion thereof being tapered towards the lower edge of the main portion.

42. A method for treating abdominal aortic aneurysms by installing inside the aorta the graft of claim 35, the method comprising the steps of:

placing the main graft portion inside the aorta whereby the portion is firmly retained against the upper aortic neck with a lower edge of the graft main portion freely moving inside the aneurysm, inserting the upper end of the leg portion inside the lower portion of the main graft portion, and expanding the anchoring means of the leg portion once the anchoring means are at least partially inside the lower portion of the graft main portion, whereby the anchoring means defining, in the expanded condition, and in at least a section thereof upwardly the inelastic edge, a maximum diameter larger than the predetermined maximum diameter of the inelastic edge, whereby the upper end of the leg portion may be retained within the lower portion of the main portion by the anchoring means, with the inelastic edge encircling the upper end of the graft leg portion and the anchoring means remaining, at least partially, within the graft main portion upwardly of the inelastic edge.

* * * * *